(12) United States Patent
Iwata et al.

(10) Patent No.: US 11,746,109 B2
(45) Date of Patent: Sep. 5, 2023

(54) CRYSTALLINE FORMS OF 2-[(2S)-1-AZABICYCLO[2.2.2]OCT-2-YL]-6-(3-METHYL-1H-PYRAZOL-4-YL)THIE-NO[3,2-D]PYRIMIDIN-4(3H)-ONE HEMIHYDRATE

(71) Applicant: TAKEDA PHARMACEUTICAL COMPANY LIMITED, Osaka (JP)

(72) Inventors: Kentaro Iwata, Kanagawa (JP); Masahiro Mizuno, Osaka (JP); Kazuhiro Maeda, Osaka (JP); Tsuneo Yasuma, Osaka (JP); Misaki Homma, Kanagawa (JP); Yuya Oguro, Kanagawa (JP); Naohiro Taya, Kanagawa (JP); Lei Zhu, Bedford, MA (US); John Daniel Bailey, Cambridge, MA (US); Marianne Langston, Cambridge, MA (US); Siddhesh Dinanath Patil, Cambridge, MA (US); Shruti Gour, Watertown, MA (US); Lilly Roy, Boston, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 895 days.

(21) Appl. No.: 16/088,096

(22) PCT Filed: Mar. 27, 2017

(86) PCT No.: PCT/US2017/024226
§ 371 (c)(1),
(2) Date: Sep. 25, 2018

(87) PCT Pub. No.: WO2017/172565
PCT Pub. Date: Oct. 5, 2017

(65) Prior Publication Data
US 2023/0102273 A1 Mar. 30, 2023

Related U.S. Application Data

(60) Provisional application No. 62/367,842, filed on Jul. 28, 2016, provisional application No. 62/314,080, filed on Mar. 28, 2016.

(51) Int. Cl.
*C07D 471/08* (2006.01)
*A61K 9/48* (2006.01)

(52) U.S. Cl.
CPC ............ *C07D 471/08* (2013.01); *A61K 9/485* (2013.01); *A61K 9/4858* (2013.01); *C07B 2200/13* (2013.01)

(58) Field of Classification Search
CPC .... C07D 471/08; A61K 9/485; A61K 9/4858; C07B 2200/13
See application file for complete search history.

(56) References Cited

FOREIGN PATENT DOCUMENTS

| | | | | |
|---|---|---|---|---|
| EP | 2540728 A1 | * | 1/2013 | ........... A61K 31/519 |
| EP | 2540728 A1 | | 1/2013 | |

OTHER PUBLICATIONS

Caira, M.R., "Crystalline Polymorphism of Organic Compounds", Topics in Current Chemistry, Springer, Berlin, DE, vol. 198, Jan. 1998, pp. 163-208.

* cited by examiner

*Primary Examiner* — Michael Barker
*Assistant Examiner* — Jed A Kucharczk
(74) *Attorney, Agent, or Firm* — Honigman LLP; Lucy X. Yang; Jonathan P. O'Brien

(57) ABSTRACT

The present disclosure relates to crystalline forms of 2-[(2S)-1-azabicyclo[2.2.2]oct-2-yl]-6-(3-methyl-1H-pyrazol-4-yl)thieno[3,2-d]pyrimidin-4(3H)-one hemihydrate (Compound 1) and/or tautomers thereof, wherein Compound 1 has the structure: (I)·0.5H$_2$O; processes for preparing crystalline forms of Compound 1 and/or tautomers thereof; pharmaceutical compositions comprising the crystalline forms; methods of inhibiting a cell division cycle 7 in a mammal comprising administering the crystalline forms; and methods of treating a cell division cycle 7 mediated cancer in a mammal comprising administering the crystalline forms or a pharmaceutical composition comprising the crystalline forms.

20 Claims, 9 Drawing Sheets

(I)

FIG. 2    13C ssNMR spectrum for Compound 1 Crystalline Form I

Overlay of 13C ssNMR spectra for Compound 1 Crystalline Form A and Compound 1 Crystalline Form I

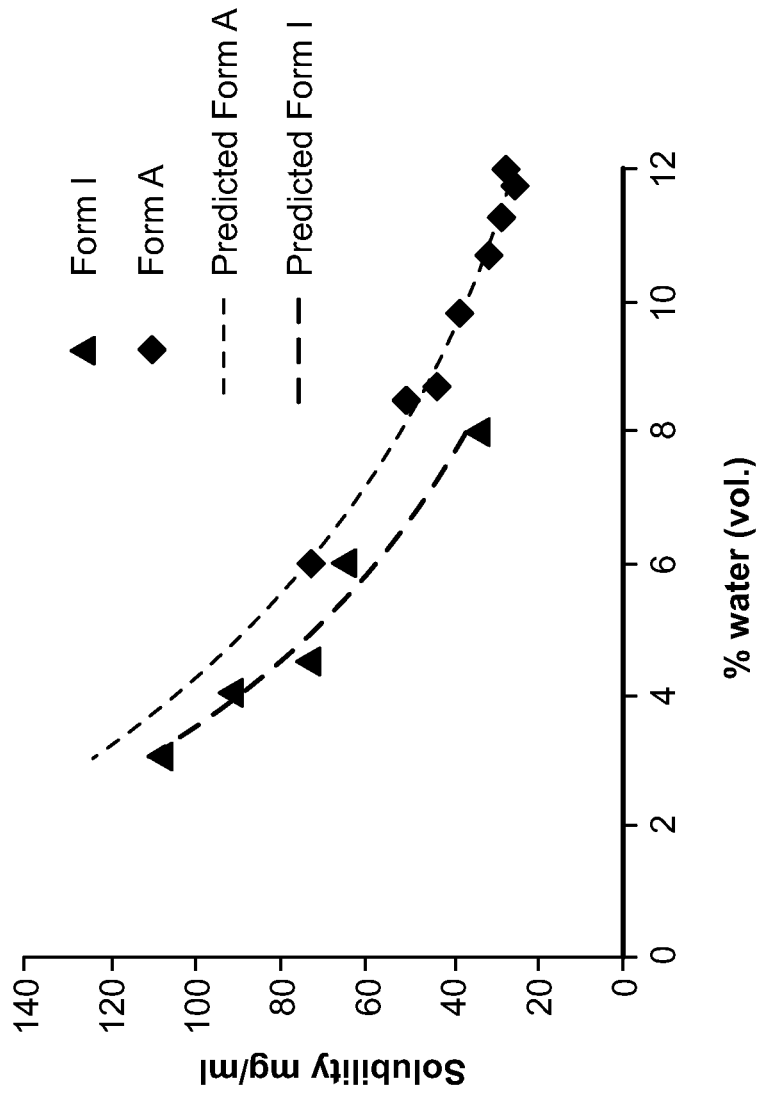

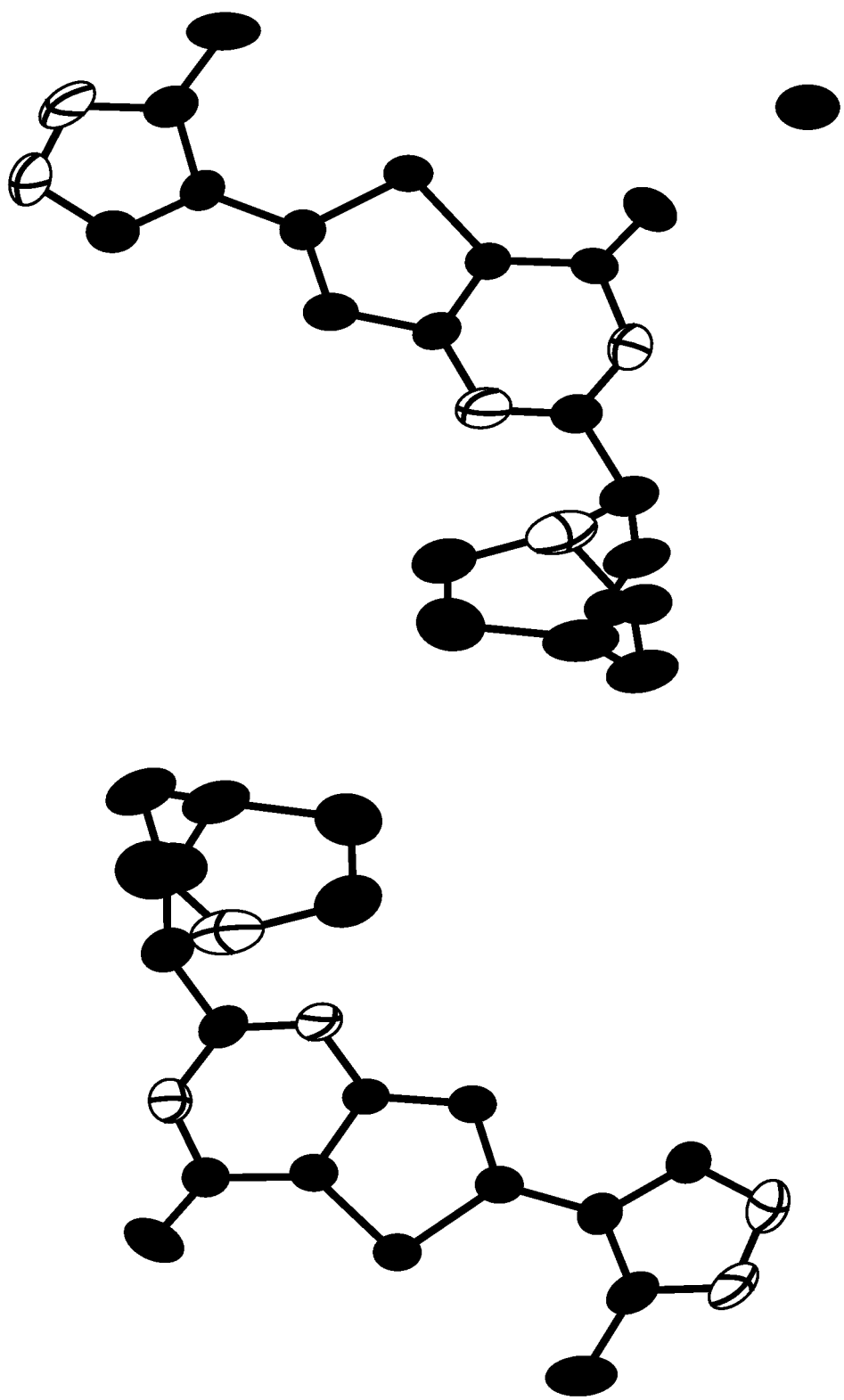
FIG. 8  ORTEP Figure of the Compound 1 Crystalline Form I Crystal Structure with Hydrogen Atoms Omitted.

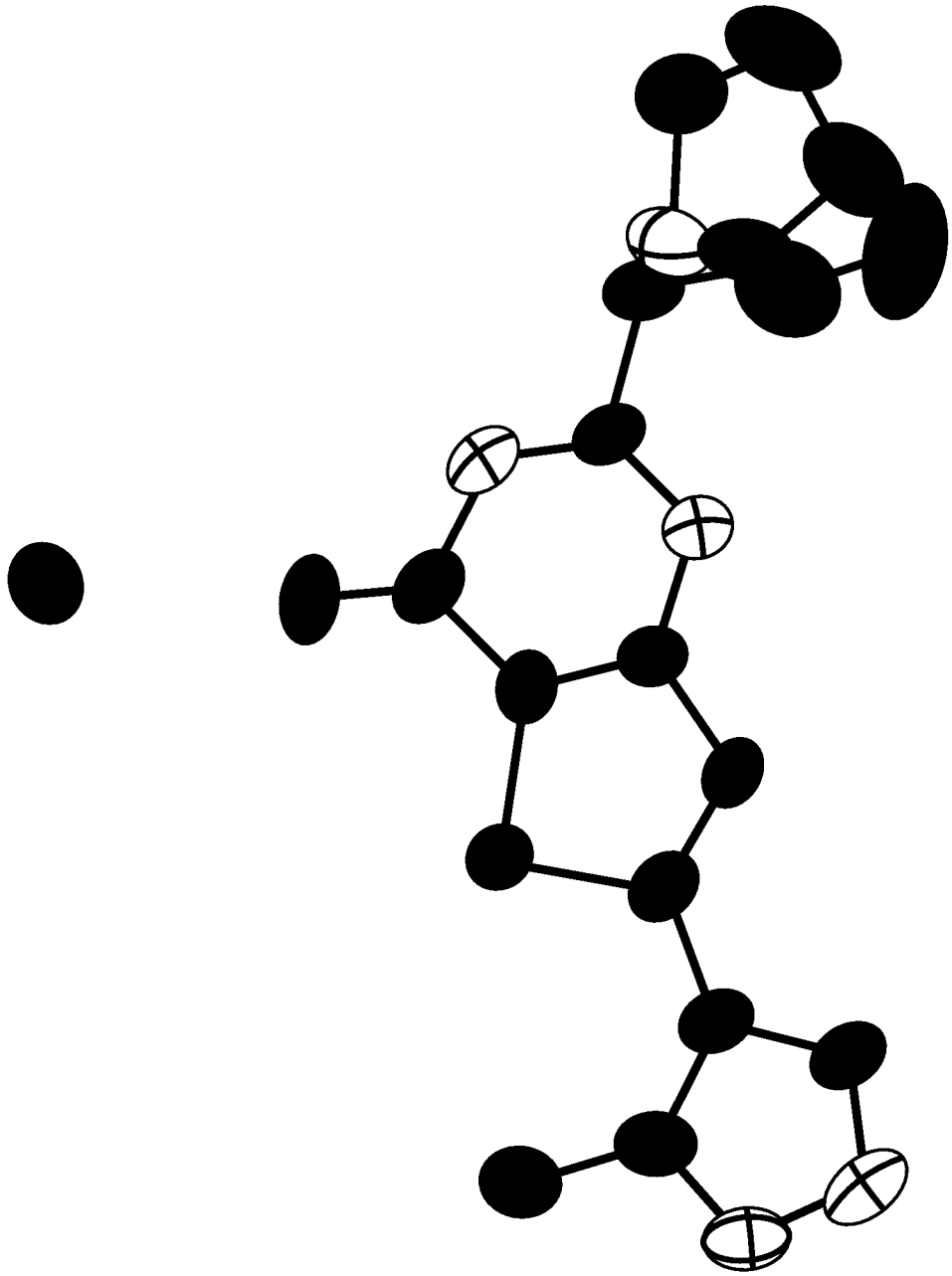
FIG. 9 ORTEP Figure of the Compound 1 Crystalline Form A Crystal Structure with Hydrogen Atoms Omitted.

CRYSTALLINE FORMS OF 2-[(2S)-1-AZABICYCLO[2.2.2]OCT-2-YL]-6-(3-METHYL-1H-PYRAZOL-4-YL)THIENO[3,2-D]PYRIMIDIN-4(3H)-ONE HEMIHYDRATE

CROSS-REFERENCE TO RELATED APPLICATIONS

This application is a 35 U.S.C. § 371 United States National Phase Application of, and claims priority to, PCT Application No.: PCT/US2017/024226, filed Mar. 27, 2017, which claims the benefit under 35 U.S.C. § 119 of U.S. Provisional Application Ser. No. 62/367,842, filed Jul. 28, 2016, and U.S. Provisional Application Ser. No. 62/314,080, filed Mar. 28, 2016. The entire contents of the aforesaid applications are incorporated by reference herein in its entirety.

FIELD

The present disclosure relates to crystalline forms of compound 2-[(2S)-1-azabicyclo[2.2.2]oct-2-yl]-6-(3-methyl-1H-pyrazol-4-yl)thieno[3,2-d]pyrimidin-4(3H)-one hemihydrate (Compound 1) and/or tautomers thereof, wherein Compound 1 has the structure:

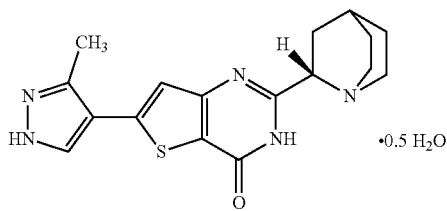

The disclosure also relates to processes for preparing crystalline forms of Compound 1 and/or tautomers thereof. The disclosure further relates to pharmaceutical compositions comprising crystalline Compound 1 and/or tautomers thereof, methods of inhibiting a cell division cycle 7 (Cdc7) in a mammal comprising administering crystalline Compound 1 and/or tautomers thereof, as well as methods of treating a cell division cycle 7 mediated cancer in a mammal.

A characteristic of cancer is abnormal cell proliferation with a broken control mechanism. Most cancer cells grow more rapidly than cells of normal tissues. During cell division cycle, chromosome duplication is essential, and replication of DNA in the S phase of the cell division cycle is tightly regulated. Inhibition of DNA replication has been confirmed to be an effective therapy for cancer treatment and, for example, DNA replication inhibitors such as hydroxyurea (HU), gemcitabine and active metabolites of 5-fluorouracil are widely used as therapeutic agents for the treatment of cancer in clinical practice.

Cdc7 is an evolutionarily well-conserved serine/threonine kinase and is known to play an important role in the initiation of DNA replication. The kinase activity of Cdc7 is controlled by binding with its activating partner. From the late stage of G1 phase to S phase, Cdc7 forms a complex with Dbf4 (also known as ASK) and phosphorylates the Cdc7 substrate to control transition from the G1 phase to the S phase. Recent studies have reported that Cdc7 plays important roles in both DNA replication and DNA damage signaling pathways.

In recent years, Cdc7 has been considered an attractive target for the treatment of cancer. Overexpression of Cdc7 is observed in many cancer cell lines and clinical tumors, including tumors associated with breast cancer, colorectal cancer, and lung cancer. In some cancer cell lines, an increase in chromosomal copy number of an activating factor, Dbf4, is found. Interestingly, a cancer cell line and an untransformed fibroblast cell line show different responses to suppression of Cdc7 expression using siRNA. The suppression of Cdc7 expression using siRNA causes the S phase arrest in cancer cell lines and induces apoptosis, whereas in normal cells it induces the G1 phase arrest in a p53 activity-dependent manner. Furthermore, Cdc7 is activated in cells undergoing replication stress, and apoptosis induced by hydroxyurea and etoposide increases in Cdc7 down-regulated cells. Accordingly, a Cdc7 inhibitor, as a single agent or in combination with other chemotherapeutic agents, could be useful for a selective cancer treatment.

Homma M. et al., U.S. Pat. No. 8,722,660 B2, a national stage entry of PCT/JP2011/053303 (published as WO 2011/102399), discloses compounds which are effective inhibitors of Cdc7. The compounds are useful for inhibiting Cdc7 kinase activity in vitro and in vivo and are useful for the treatment of disorders of cell proliferation, particularly cancer.

U.S. Pat. No. 8,722,660 B2 additionally discloses pharmaceutical compositions containing these compounds, and methods for the treatment or therapy of diseases, disorders, or conditions associated with Cdc7 kinase, including proliferative diseases such as cancer.

The synthesis of 2-[(2S)-1-azabicyclo[2.2.2]oct-2-yl]-6-(3-methyl-1H-pyrazol-4-yl)thieno[3,2-d]pyrimidin-4(3H)-one and/or tautomers thereof (crude Compound 1) was described in Example 178 of U.S. Pat. No. 8,722,660 B2. The large-scale manufacturing of a pharmaceutical composition poses many challenges to the chemist and chemical engineer. While many of these challenges relate to the handling of large quantities of reagents and control of large-scale reactions, the production and handling of the final active product poses special challenges linked to the nature of the final crystalline form, also referred to herein as the pharmaceutically active substance. Not only should the active product be prepared in high yield, be stable, and be capable of ready isolation, but the manufacturing processes must also be controlled such that the desired crystalline form is produced reliably and consistently. The stability and purity of the crystalline form of the pharmaceutical preparation must be considered during each step of the manufacturing process, including the synthesis, isolation, bulk storage, pharmaceutical formulation and long-term storage.

The pharmaceutically active substance used to prepare pharmaceutical compositions should be as pure as possible, and its stability on long-term storage should be guaranteed under various environmental conditions. These properties are useful to prevent the appearance of unintended degradation products in pharmaceutical compositions, as degradation products may be potentially toxic or result simply in reducing the potency of the composition.

One primary concern for the large-scale manufacture of pharmaceutical compounds is that the active substance should have a stable crystalline polymorph to ensure consistent processing parameters and pharmaceutical quality. If an unstable crystalline form is used, crystal polymorph may change during manufacture and/or storage, resulting in quality control problems and formulation irregularities. Such a change may affect the reproducibility of the manufacturing process, resulting in final formulations which do not meet the high quality and stringent requirements imposed on formulations of pharmaceutical compositions. In this regard, it should be generally noted that any change to the solid state of a pharmaceutical composition which can improve its physical and chemical stability imparts a significant advantage over less stable forms of the same drug. Furthermore, it is critical that a robust manufacturing process is developed that consistently produces the active substance. The existence of multiple crystalline forms with close solubilities creates a difficult challenge in large-scale manufacture of pharmaceutical compounds.

When a compound crystallizes from a solution or slurry, it may crystallize with different spatial lattice arrangements, a property referred to as "polymorphism." Each of the crystal forms is known as a "polymorph." While polymorphs of a given substance have the same chemical composition, they may differ from each other with respect to one or more physical properties, such as solubility, dissociation, true density, dissolution, melting point, crystal shape, compaction behavior, flow properties, and/or solid state stability.

As described generally above, the polymorphic behavior of drugs can be of great importance in pharmacology. The differences in physical properties exhibited by polymorphs affect practical parameters such as storage stability, compressibility and density (important in formulation and product manufacturing), as well as dissolution rates (an important factor in determining bio-availability). Differences in stability can result from changes in chemical reactivity (e.g., differential oxidation, such that a dosage form discolors more rapidly when it is one polymorph than when it is another polymorph), mechanical changes (e.g., tablets crumble on storage as a kinetically favored polymorph converts to a thermodynamically more stable polymorph), or both (e.g., tablets of one polymorph are more susceptible to breakdown at high humidity). In addition, the physical properties of the crystal may be important in processing. For instance, one polymorph might be more likely to form solvates that cause the solid form to aggregate and increase the difficulty of solid handling. Alternatively, the particle shape and size distribution might be different between one polymorph relative to another, leading to increased challenges when filtering the pharmaceutically active substance to remove impurities.

While drug formulations having improved chemical and physical properties are desired, there is no predictable means for preparing new drug forms (e.g., polymorphs and other new crystalline forms) of existing molecules for such formulations. These new forms would provide consistency in physical properties over a range of environments common to manufacturing and composition usage. Thus, there is a need for new drug forms that are useful for inhibiting Cdc7 kinase activity in vitro and in vivo, and are useful for the treatment of disorders of cell proliferation, particularly cancer, and other disorders associated with Cdc7 kinase activity, as well as have properties suitable for large-scale manufacturing and formulation.

The present disclosure relates to crystalline 2-[(2S)-1-azabicyclo[2.2.2]oct-2-yl]-6-(3-methyl-1H-pyrazol-4-yl)thieno[3,2-d]pyrimidin-4(3H)-one hemihydrate (Compound 1) and/or tautomers thereof, wherein Compound 1 has the structure:

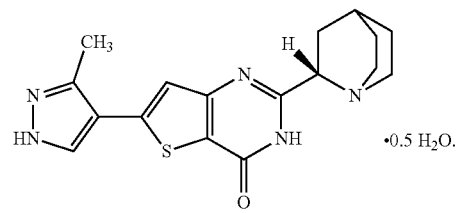 [SMILES: Cc1n[nH]cc1-c1cc2nc([C@@H]3CC4CCN3CC4)[nH]c(=O)c2s1]

These forms have properties that are useful for large-scale manufacturing, pharmaceutical formulation, and/or storage. The present disclosure also relates to pharmaceutical compositions comprising crystalline Compound 1 and/or tautomers thereof and to methods of use of said compound, including the treatment of several diseases, disorders or conditions as described herein.

Some embodiments of the disclosure relate to a pharmaceutical composition comprising a pharmaceutically acceptable carrier or diluent; and crystalline Compound 1 and/or tautomers thereof.

Some embodiments of the disclosure relate to methods of treating a subject in need of a Cdc7 kinase inhibitor, by administering an effective amount of crystalline Compound 1 and/or tautomers thereof.

Some embodiments of the disclosure relate to said methods, wherein the compound is Compound 1 Crystalline Form I. Some additional embodiments of the disclosure relate to said methods, wherein the compound is Compound 1 Crystalline Form A. Some additional embodiments of the disclosure relate to said methods, wherein the compound is a mixture of Compound 1 Crystalline Form I and Compound 1 Crystalline Form A.

Some embodiments of the disclosure relate to methods of preparing crystalline forms of Compound 1 and/or tautomers thereof. Some embodiments of the disclosure are directed to said methods, wherein the compound is Compound 1 Crystalline Form I. Some additional embodiments of the disclosure are directed to said methods, wherein the compound is Compound 1 Crystalline Form A. Some additional embodiments of the disclosure relate to said methods, wherein the compound is a mixture of Compound 1 Crystalline Form I and Compound 1 Crystalline Form A.

BRIEF DESCRIPTION OF THE DRAWINGS

In the descriptions that follow, "XRPD" means X-ray powder diffraction, "ssNMR" means solid state nuclear magnetic resonance, and "ORTEP" means Oak Ridge Thermal Ellipsoid Program.

FIG. 7 shows the solubility of Compound 1 Crystalline Form I and Compound 1 Crystalline Form A in water/DMSO at 60° C.

FIG. 8 is an ORTEP figure of the Compound 1 Crystalline Form I crystal structure with hydrogen atoms omitted.

FIG. 9 is an ORTEP figure of the Compound 1 Crystalline Form A crystal structure with hydrogen atoms omitted.

DETAILED DESCRIPTION

Definitions and Abbreviations

Figure 1:
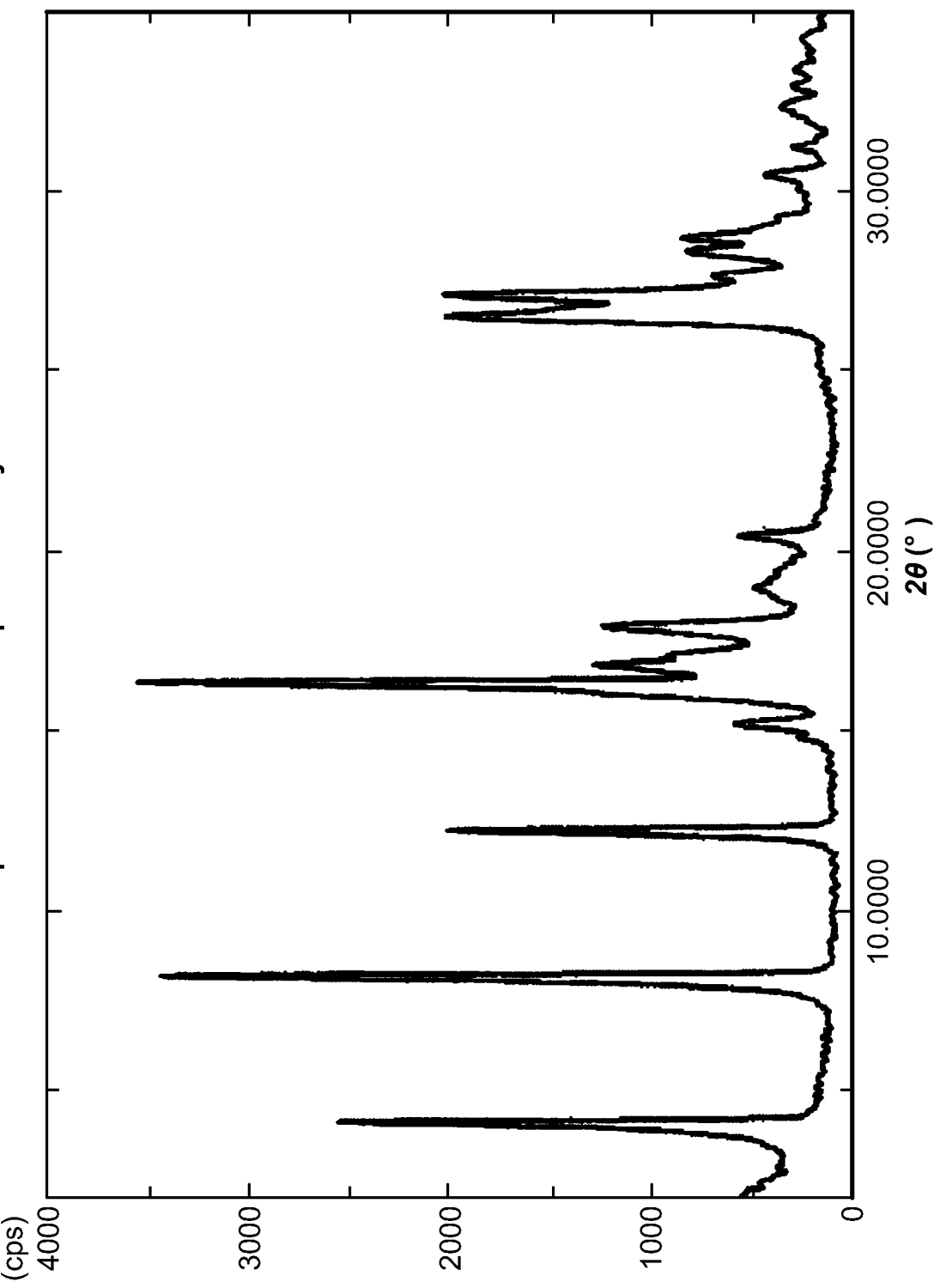
FIG. 1 is an XRPD pattern of Compound 1 Crystalline Form 1.

As used above, and throughout the description, the following terms, unless otherwise indicated, shall be understood to have the following meanings.

As used herein, the "wt %" and "% by weight" are used interchangeably and refer to weight percent.

As used herein, the terms "crystalline compound," "compound," and "crystalline form of a compound" are used interchangeably.

As used herein, the terms "crystalline form of Compound 1" and "crystalline Compound 1" are used interchangeably.

As used herein, the terms "a crude preparation of Compound 1" and "crude Compound 1" refer to 2-[(2S)-1-azabicyclo[2.2.2]oct-2-yl]-6-(3-methyl-1H-pyrazol-4-yl)thieno[3,2-d]pyrimidin-4(3H)-one and/or tautomers thereof. The synthesis of crude Compound 1 was described in Example 178 of U.S. Pat. No. 8,722,660 B2. As a non-limiting example, tautomerization of crude Compound 1 may occur in the pyrazole and pyrimidine groups of crude Compound 1. Specific examples of tautomerization that may occur in crude Compound 1 include:

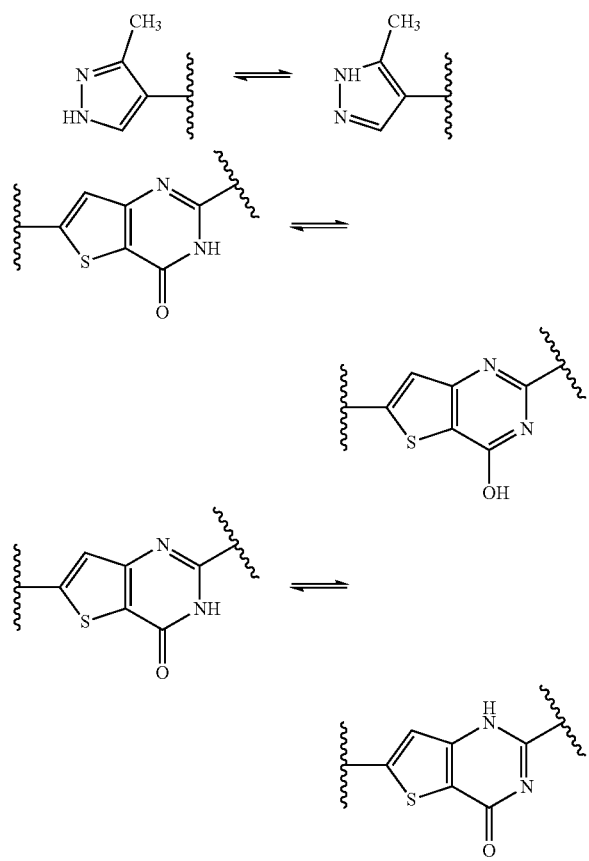

Specific non-limiting examples of isomeric structures of the tautomers included are:

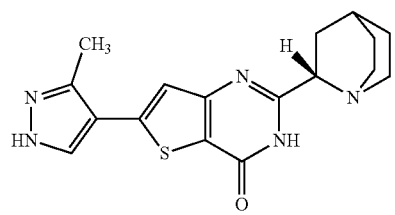 [SMILES: Cc1n[nH]cc1-c1cc2nc([C@@H]3CC4CCN3CC4)[nH]c(=O)c2s1]

2-[(2S)-1-azabicyclo[2.2.2]oct-2-yl]-6-(3-methyl-1H-pyrazol-4-yl)thieno[3,2-d]pyrimidin-4(3H)-one, and

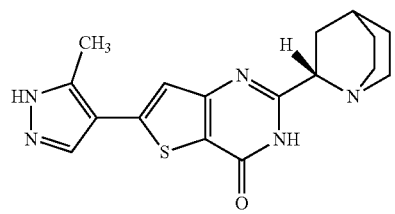 [SMILES: Cc1[nH]ncc1-c1cc2nc([C@@H]3CC4CCN3CC4)[nH]c(=O)c2s1]

2-[(2S)-1-azabicyclo[2.2.2]oct-2-yl]-6-(5-methyl-1H-pyrazol-4-yl)thieno[3,2-d]pyrimidin-4(3H)-one.

As used herein, the terms "Form I" and "Compound 1 Crystalline Form I" are used interchangeably, and describe crystalline Form I of 2-[(2S)-1-azabicyclo[2.2.2]oct-2-yl]-6-(3-methyl-1H-pyrazol-4-yl)thieno[3,2-d]pyrimidin-4 (3H)-one hemihydrate (Compound 1) and/or tautomers thereof, as characterized in some embodiments by the data shown in FIGS. 1, 2, 7, and 8.

As used herein, the terms "Form A" and "Compound 1 Crystalline Form A" are used interchangeably, and describe crystalline Form A of 2-[(2S)-1-azabicyclo[2.2.2]oct-2-yl]-6-(3-methyl-1H-pyrazol-4-yl)thieno[3,2-d]pyrimidin-4 (3H)-one hemihydrate (Compound 1) and/or tautomers thereof, as characterized in some embodiments by the data shown in FIGS. 3, 4, 7, and 9.

As used herein, the terms "Form A/I" and "Compound 1 Crystalline Form A/I" are used interchangeably, and describe a mixture of Compound 1 Crystalline Form A and Compound 1 Crystalline Form I.

As used herein, "crystalline" refers to a solid in which the constituent atoms, molecules, or ions are packed in a regularly ordered, repeating three-dimensional pattern having a highly regular chemical structure. For the purposes of this application, the terms "crystalline form" and "polymorph" are synonymous; the terms distinguish between crystals that have different properties (e.g., different XRPD patterns, different DSC scan results, or different $^{13}C$ solid state NMR patterns).

As used herein, "substantially crystalline" refers to solid forms of Compound 1 and/or tautomers thereof that are at least a particular weight percent crystalline. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%. In some embodiments, substantially crystalline refers to solid forms that are at least 70% crystalline. In some embodiments, substantially crystalline refers to solid forms that are at least 80% crystalline. In some embodiments, substantially crystalline refers to solid forms that are at least 85% crystalline. In some embodiments, substantially crystalline refers to solid forms that are at least 90% crystalline.

In some embodiments, substantially crystalline refers to solid forms that are at least 95% crystalline.

As used herein, the term "hydrate" refers to a solvate wherein the solvent molecule is H$_2$O that is present in a defined stoichiometric amount of at least 1:1 water: 2-[(2S)-1-azabicyclo[2.2.2]oct-2-yl]-6-(3-methyl-1H-pyrazol-4-yl)thieno[3,2-d]pyrimidin-4(3H)-one and/or tautomers thereof, and includes, for example, monohydrates, dihydrates, and trihydrates.

As used herein, the term "hemihydrate" refers to a solvate wherein the solvent molecule is H$_2$O that is present in a defined stoichiometric amount of 0.5:1 water: 2-[(2S)-1-azabicyclo[2.2.2]oct-2-yl]-6-(3-methyl-1H-pyrazol-4-yl)thieno[3,2-d]pyrimidin-4(3H)-one and/or tautomers thereof.

As used herein, the term "dose strength" refers to the amount of a specific compound present in a dosage form.

As used herein, the term "mixture" refers to the combined elements of the mixture regardless of the phase-state of the combination (e.g., liquid or liquid/crystalline).

As used herein, the term "seeding" refers to the addition of crystalline material to a solution or mixture to initiate crystallization.

As used herein, the particle size distribution term "D10" refers to the particle diameter at which 10% of a sample's mass is composed of particles of a smaller diameter than the D10 diameter.

As used herein, the particle size distribution term "D50" refers to the particle diameter at which 50% of a sample's mass is composed of particles of a smaller diameter than the D50 diameter.

As used herein, the particle size distribution term "D90" refers to the particle diameter at which 90% of a sample's mass is composed of particles of a smaller diameter than the D90 diameter.

As used herein, the phrases "crystalline Compound 1 and/or tautomers thereof" and the like are all understood to mean a crystalline Compound 1 and all of its tautomeric forms. As a non-limiting example, tautomerization of crystalline Compound 1 may occur in the pyrazole and pyrimidine groups of crystalline Compound 1. Specific examples of tautomerization that may occur in Compound 1 include:

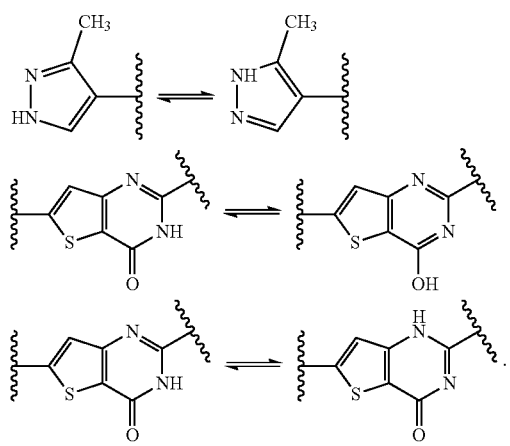

Specific non-limiting examples of isomeric structures of the tautomers included are:

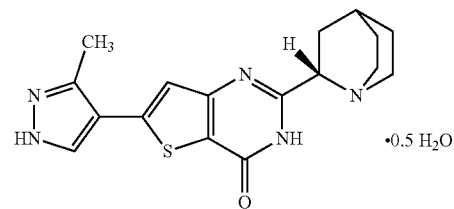 [SMILES: Cc1n[nH]cc1-c1cc2nc([C@@H]3CC4CCN3CC4)[nH]c(=O)c2s1]

2-[(2S)-1-azabicyclo[2.2.2]oct-2-yl]-6-(3-methyl-1H-pyrazol-4-yl)thieno[3,2-d]pyrimidin-4(3H)-one hemihydrate, and

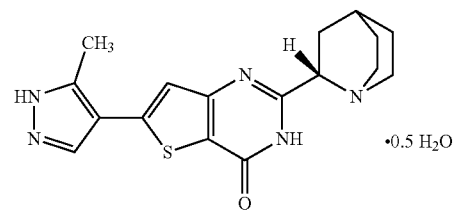 [SMILES: Cc1[nH]ncc1-c1cc2nc([C@@H]3CC4CCN3CC4)[nH]c(=O)c2s1]

2-[(2S)-1-azabicyclo[2.2.2]oct-2-yl]-6-(5-methyl-1H-pyrazol-4-yl)thieno[3,2-d]pyrimidin-4(3H)-one hemihydrate.

In one aspect, the present disclosure is related to crystalline 2-[(2S)-1-azabicyclo[2.2.2]oct-2-yl]-6-(3-methyl-1H-pyrazol-4-yl)thieno[3,2-d]pyrimidin-4(3H)-one hemihydrate (Compound 1) and/or tautomers thereof, wherein Compound 1 has the structure:

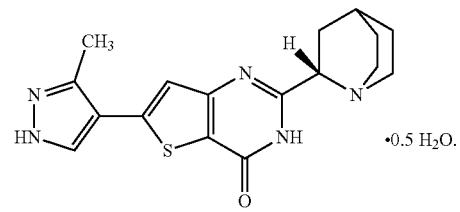 [SMILES: Cc1n[nH]cc1-c1cc2nc([C@@H]3CC4CCN3CC4)[nH]c(=O)c2s1]

Provided herein is an assortment of characterizing information to describe crystalline forms of Compound 1. It should be understood, however, that not all such information is required for one skilled in the art to determine that a particular form is present in a given composition. The determination of a particular form can be achieved using any portion of the characterizing information that one skilled in the art would recognize as sufficient for establishing the presence of a particular form, e.g., even a single distinguishing peak can be sufficient for one skilled in the art to appreciate that such particular form is present.

At least one of the crystalline forms of the disclosure has properties that make the solid forms suitable for large-scale pharmaceutical formulation manufacture. At least one of the crystalline forms can provide desirable physical and chemical properties, including low hygroscopicity and chemical and optical stability. As a nonlimiting example, both Compound 1 Crystalline Form I and Compound 1 Crystalline Form A are not hygroscopic at 25° C. or at 40° C. As a further nonlimiting example, both Compound 1 Crystalline Form I and Compound 1 Crystalline Form A are chemically and optically stable at 60° C./75% relative humidity (open) for at least eight weeks. As a further nonlimiting example, both Compound 1 Crystalline Form I and Compound 1

Crystalline Form A are chemically and optically stable at 80° C. (closed) for at least eight weeks.

Some embodiments of the disclosure are directed to the solid forms of Compound 1 and/or tautomers thereof, wherein at least a particular percentage by weight of the solid form is crystalline. In some embodiments, the solid form of Compound 1 and/or tautomers thereof is substantially crystalline. Non-limiting examples of a crystalline or substantially crystalline form of Compound 1 include Compound 1 Crystalline Form I and Compound 1 Crystalline Form A. Some embodiments of the disclosure are also directed to a solid form of Compound 1 and/or tautomers thereof, wherein at least a particular percentage by weight of the solid form is crystalline, that excludes one or more designated crystalline forms from a particular weight percentage of the solid form. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%. When a particular percentage by weight of the solid form is crystalline, the remainder of the solid form is the amorphous form of Compound 1 and/or tautomers thereof.

Other embodiments of the disclosure are directed to Compound 1 and/or tautomers thereof being a crystalline form, or being substantially a crystalline form. The crystalline form may be a particular percentage by weight of the crystalline Compound 1. Particular weight percentages include 10%, 20%, 30%, 40%, 50%, 60%, 70%, 75%, 80%, 85%, 87%, 88%, 89%, 90%, 91%, 92%, 93%, 94%, 95%, 96%, 97%, 98%, 99%, 99.5% and 99.9%. When a particular percentage by weight of Compound 1 and/or tautomers thereof is a designated crystalline form, the remainder of the Compound 1 is some combination of the amorphous form of Compound 1, and one or more crystalline forms of Compound 1 excluding the designated crystalline form. In some embodiments, the solid form of Compound 1 and/or tautomers thereof is at least 95% by weight of a crystalline form. In some embodiments, the solid form of Compound 1 and/or tautomers thereof is at least 90% by weight of a crystalline form. In some embodiments, the solid form of Compound 1 and/or tautomers thereof is at least 85% by weight of a crystalline form. In some embodiments, the solid form of Compound 1 and/or tautomers thereof is at least 80% by weight of a crystalline form.

In the following description of solid forms of Compound 1, embodiments of the disclosure may be described with reference to a particular crystalline form of Compound 1 and/or tautomers thereof, as characterized by one or more properties as discussed herein. The descriptions characterizing the crystalline forms may also be used to describe the mixture of different crystalline forms that may be present in a crystalline form of Compound 1. However, the particular crystalline forms of Compound 1 may also be characterized by one or more of the characteristics of the polymorph as described herein, with or without regard to referencing a particular crystalline form.

For analyzing a particular crystalline form, X-ray powder diffraction (XRPD) crystallographic analysis is commonly used. Throughout the specification and claims, when a crystalline form of Compound 1 and/or tautomers thereof is identified using one or more XRPD characteristic peaks given as angles 2θ, each of the 2θ values is understood to mean the given value ±0.2 degrees. It is noted that XRPD values (especially, a value in the low angle side (d-value is large) may shift slightly depending on the pulverization state of the sample.

Throughout the specification and claims, when a crystalline form of Compound 1 and/or tautomers thereof is identified using one or more XRPD characteristic peaks given as interplanar spacings (d), each of the d values is understood to mean the given value ±0.2 Angstroms.

Throughout the specification and claims, when a crystalline form of Compound 1 and/or tautomers thereof is identified using one or more $^{13}$C NMR characteristic peaks expressed in ppm, each of the ppm values is understood to mean the given value ±0.5 ppm.

In some embodiments, the present disclosure provides crystalline compound 2-[(2S)-1-azabicyclo[2.2.2]oct-2-yl]-6-(3-methyl-1H-pyrazol-4-yl)thieno[3,2-d]pyrimidin-4 (3H)-one hemihydrate (Compound 1) and/or tautomers thereof, wherein Compound 1 has the structure

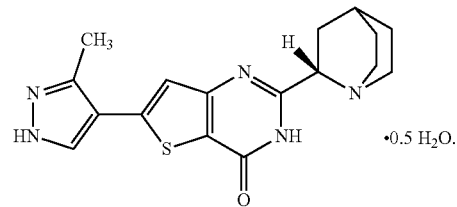 [SMILES: Cc1n[nH]cc1-c1cc2nc([C@@H]3CC4CCN3CC4)[nH]c(=O)c2s1]

·0.5 H$_2$O.

In some embodiments, crystalline Compound 1 is characterized by an X-ray powder diffraction pattern having characteristic peaks expressed in degrees 2θ at 4.1±0.2, 8.1±0.2, 12.2±0.2, and 16.3±0.2. In further embodiments, crystalline Compound 1 is characterized by an X-ray powder diffraction pattern having characteristic peaks expressed in degrees 2θ at 4.1±0.2, 8.1±0.2, 12.2±0.2, 16.3±0.2, 17.8±0.2, 26.4±0.2, and 27.0±0.2.

In some other embodiments, crystalline Compound 1 is characterized by an X-ray powder diffraction pattern having characteristic peaks expressed in Angstroms at interplanar spacings (d) of 21.6±0.2, 10.9±0.2, 7.3±0.2, and 5.4±0.2. In further embodiments, crystalline Compound 1 is characterized by an X-ray powder diffraction pattern having characteristic peaks expressed in Angstroms at interplanar spacings (d) of 21.6±0.2, 10.9±0.2, 7.3±0.2, 5.4±0.2, 5.0±0.2, 3.4±0.2, and 3.2±0.2.

In some other embodiments, crystalline Compound 1 is characterized by a solid-state $^{13}$C NMR pattern including characteristic peaks expressed in ppm at 159.7±0.5, 158.4±0.5, 145.1±0.5, 140.6±0.5, 135.5±0.5, 121.2±0.5, 114.5±0.5, 60.4±0.5, 53.8±0.5, 46.5±0.5, and 14.5±0.5.

In some embodiments, crystalline Compound 1 is Compound 1 Crystalline Form I. FIG. 1 shows an X-ray powder diffraction (XRPD) pattern of Compound 1 Crystalline Form I.

In some embodiments, Form I is characterized by an X-ray powder diffraction pattern having characteristic peaks expressed in degrees 2θ at 15.2±0.2, 17.8±0.2, and 27.6±0.2. In some embodiments, Form I is characterized by an X-ray powder diffraction pattern having characteristic peaks expressed in degrees 2θ at 4.1±0.2, 8.1±0.2, 12.2±0.2, 15.2±0.2, 16.3±0.2, 17.8±0.2, and 27.6±0.2. In some embodiments, Form I is characterized by an X-ray powder diffraction pattern having characteristic peaks expressed in degrees 2θ at 4.1±0.2, 8.1±0.2, 12.2±0.2, 15.2±0.2, 16.3±0.2, 17.8±0.2, 19.0±0.2, and 27.6±0.2. In some embodiments, Form I is characterized by an X-ray powder diffraction pattern having characteristic peaks expressed in degrees 2θ at 4.1±0.2, 8.1±0.2, 12.2±0.2, 15.2±0.2, 16.3±0.2, 17.8±0.2, 19.0±0.2, 20.4±0.2, 26.4±0.2, 27.0±0.2, 27.6±0.2, and 30.4±0.2.

In some embodiments, Form I is characterized by an X-ray powder diffraction pattern having characteristic peaks expressed in Angstroms at interplanar spacings (d) of 5.8±0.2, 5.0±0.2, and 3.2±0.2. In some embodiments, Form I is characterized by an X-ray powder diffraction pattern having characteristic peaks expressed in Angstroms at interplanar spacings (d) of 21.6±0.2, 10.9±0.2, 7.3±0.2, 5.8±0.2, 5.4±0.2, 5.0±0.2, and 3.2±0.2. In some embodiments, Form I is characterized by an X-ray powder diffraction pattern having characteristic peaks expressed in Angstroms at interplanar spacings (d) of 21.6±0.2, 10.9±0.2, 7.3±0.2, 5.8±0.2, 5.4±0.2, 5.0±0.2, 4.3±0.2, 3.4±0.2, 3.3±0.2, 3.2±0.2, and 2.9±0.2.

In some embodiments, Form 1 is characterized by an X-ray powder diffraction pattern substantially as depicted in FIG. 1.

Figure 2:
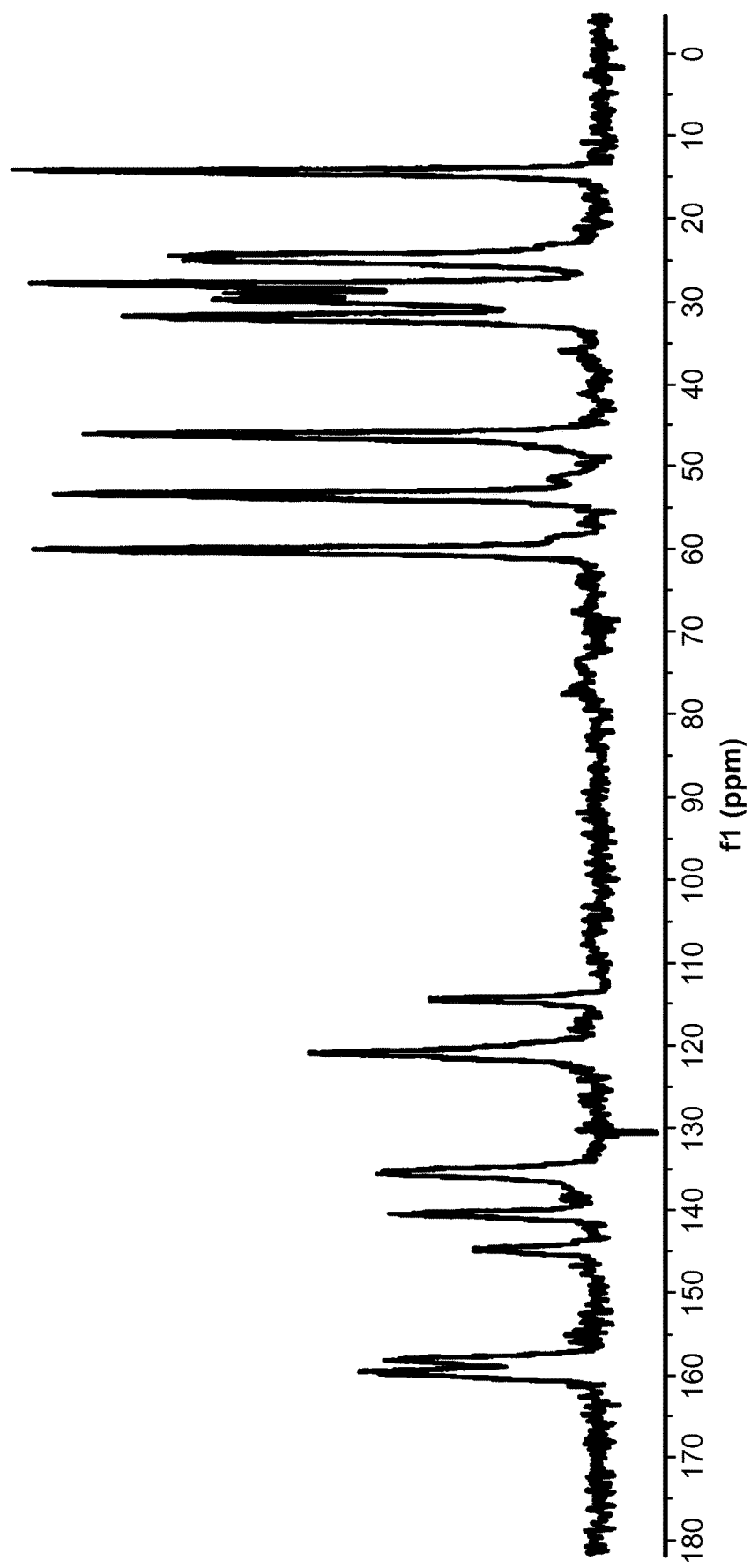
FIG. 2 is a $^{13}$C ssNMR spectrum of Compound 1 Crystalline Form I.

FIG. 2 shows a $^{13}$C ssNMR spectrum of Compound 1 Crystalline Form I.

In some embodiments, Form I is characterized by a solid-state $^{13}$C NMR pattern including characteristic peaks expressed in ppm at 32.2±0.5, 30.2±0.5, 29.3±0.5, 28.2±0.5, 25.3±0.5, and 24.8±0.5. In some embodiments, Form I is characterized by a solid-state $^{13}$C NMR pattern including characteristic peaks expressed in ppm at 159.7±0.5, 158.4±0.5, 145.1±0.5, 144.8±0.5, 140.6±0.5, 135.7±0.5, 135.3±0.5, 121.2±0.5, 114.7±0.5, 114.5±0.5, 60.4±0.5, 53.8±0.5, 46.5±0.5, 32.2±0.5, 30.2±0.5, 29.3±0.5, 28.2±0.5, 25.3±0.5, 24.8±0.5, and 14.5±0.5.

In some embodiments, Form I is characterized by a solid-state $^{13}$C NMR pattern substantially as depicted in FIG. 2.

FIG. 8 shows an ORTEP figure of the Compound 1 Crystalline Form I crystal structure with hydrogen atoms omitted.

In some embodiments, Form I is characterized by colorless crystals. In some embodiments, Form I is characterized by prism crystals. In some embodiments, Form I is characterized by a monoclinic crystal system. In some embodiments, Form I is characterized by a P2$_1$ (#4) space group. In some embodiments, Form I is characterized by the single crystal lattice parameters: a=6.2263(1) Å; b=43.5007(8) Å; c=6.7944(2) Å; β=117.207(2)°; and V=1636.65(6) Å$^3$. In some other embodiments, Form I is characterized by any of the crystallographic parameters listed in Example 14.

In some embodiments, Form I is characterized by an ORTEP figure with hydrogen atoms omitted substantially as depicted in FIG. 8.

In some embodiments, Form I is characterized by Low frequency Raman spectroscopy including characteristic peaks 17.4±0.4 cm$^{-1}$ and around 11 cm$^{-1}$ as a shoulder peak.

In some embodiments, the solubility of Form I in water/DMSO at 60° C. is substantially as depicted in FIG. 7.

In some embodiments, Form I is not hygroscopic at 25° C. In some embodiments, Form I is not hygroscopic at 40° C. In some embodiments, Form I is not hygroscopic at temperatures ranging from 25° C. to 40° C.

In some embodiments, Form I is chemically and optically stable at 80° C. (closed environment) for at least eight weeks. In some embodiments, Form I is chemically and optically stable at 60° C./75% relative humidity (open environment) for at least eight weeks.

In some embodiments, crystalline Compound 1 is Compound 1 Crystalline Form A.

Figure 3:
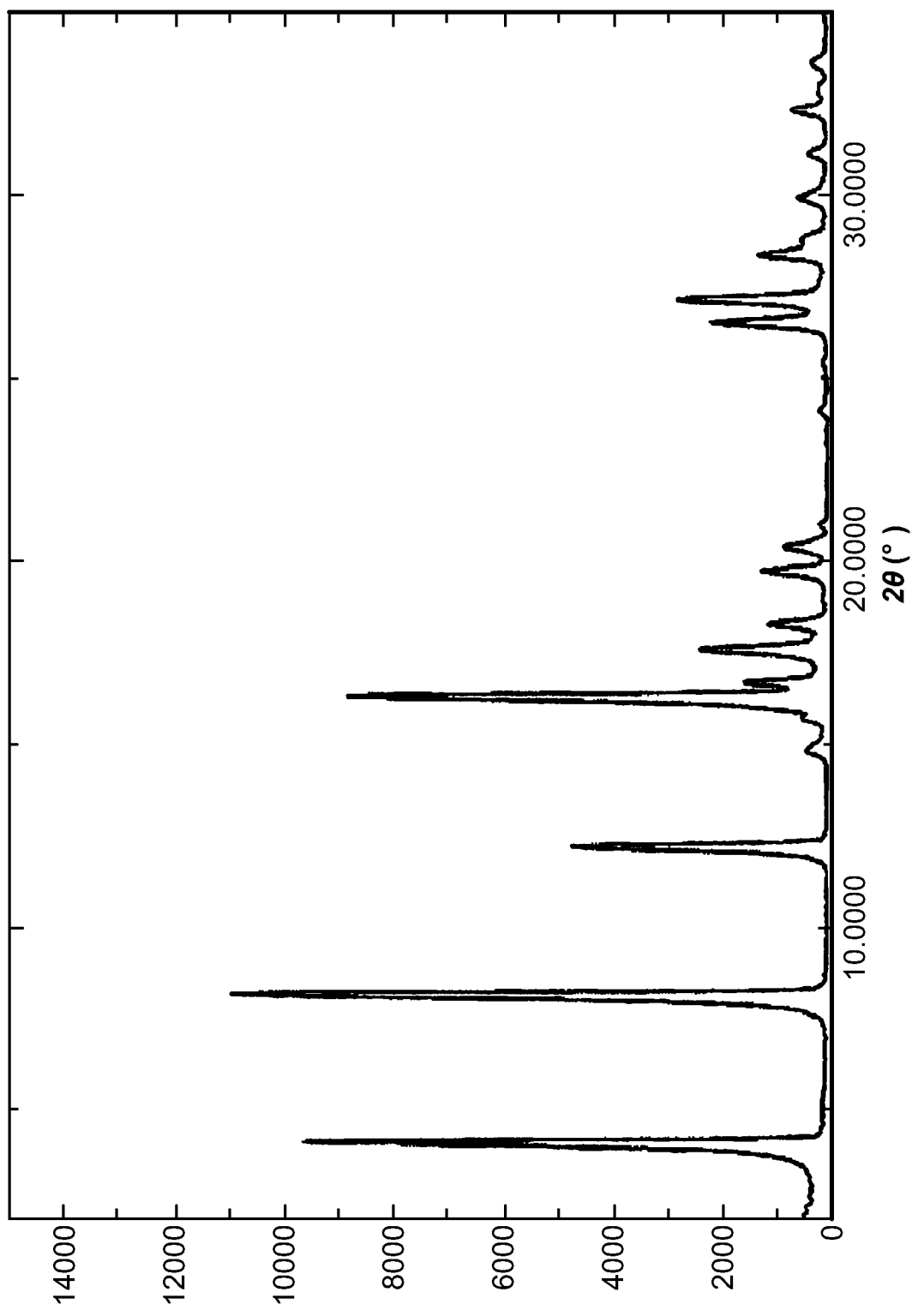
FIG. 3 is an XRPD pattern of Compound 1 Crystalline Form A.

FIG. 3 shows an X-ray powder diffraction (XRPD) pattern of Compound 1 Crystalline Form A.

In some embodiments, Form A is characterized by an X-ray powder diffraction pattern having characteristic peaks expressed in degrees 2θ at 17.6±0.2, 18.2±0.2, and 19.7±0.2. In some embodiments, Form A is characterized by an X-ray powder diffraction pattern having characteristic peaks expressed in degrees 2θ at 4.1±0.2, 8.1±0.2, 12.2±0.2, 16.3±0.2, 17.6±0.2, 18.2±0.2, and 19.7±0.2. In some embodiments, Form A is characterized by an X-ray powder diffraction pattern having characteristic peaks expressed in degrees 2θ at 4.1±0.2, 8.1±0.2, 12.2±0.2, 16.3±0.2, 17.6±0.2, 18.2±0.2, 19.7±0.2, 26.5±0.2, 27.1±0.2, and 29.9±0.2. In some embodiments, Form A is characterized by an X-ray powder diffraction pattern having characteristic peaks expressed in degrees 2θ at 4.1±0.2, 8.1±0.2, 12.2±0.2, 16.3±0.2, 17.6±0.2, 18.2±0.2, 19.7±0.2, 24.1±0.2, 26.5±0.2, 27.1±0.2, and 29.9±0.2.

In some embodiments, Form A is characterized by an X-ray powder diffraction pattern having characteristic peaks expressed in Angstroms at interplanar spacings (d) of 5.1±0.2, 4.9±0.2, and 4.5±0.2. In some embodiments, Form A is characterized by an X-ray powder diffraction pattern having characteristic peaks expressed in Angstroms at interplanar spacings (d) of 21.5±0.2, 10.9±0.2, 7.3±0.2, 5.5±0.2, 5.1±0.2, 4.9±0.2, and 4.5±0.2. In some embodiments, Form A is characterized by an X-ray powder diffraction pattern having characteristic peaks expressed in Angstroms at interplanar spacings (d) of 21.5±0.2, 10.9±0.2, 7.3±0.2, 5.5±0.2, 5.1±0.2, 4.9±0.2, 4.5±0.2, 3.4±0.2, 3.3±0.2, and 3.0±0.2. In some embodiments, Form A is characterized by an X-ray powder diffraction pattern having characteristic peaks expressed in Angstroms at interplanar spacings (d) of 21.5±0.2, 10.9±0.2, 7.3±0.2, 5.5±0.2, 5.1±0.2, 4.9±0.2, 4.5±0.2, 3.7±0.2, 3.4±0.2, 3.3±0.2, and 3.0±0.2.

In some embodiments, Form A is characterized by an X-ray powder diffraction pattern substantially as depicted in FIG. 3.

Figure 4:
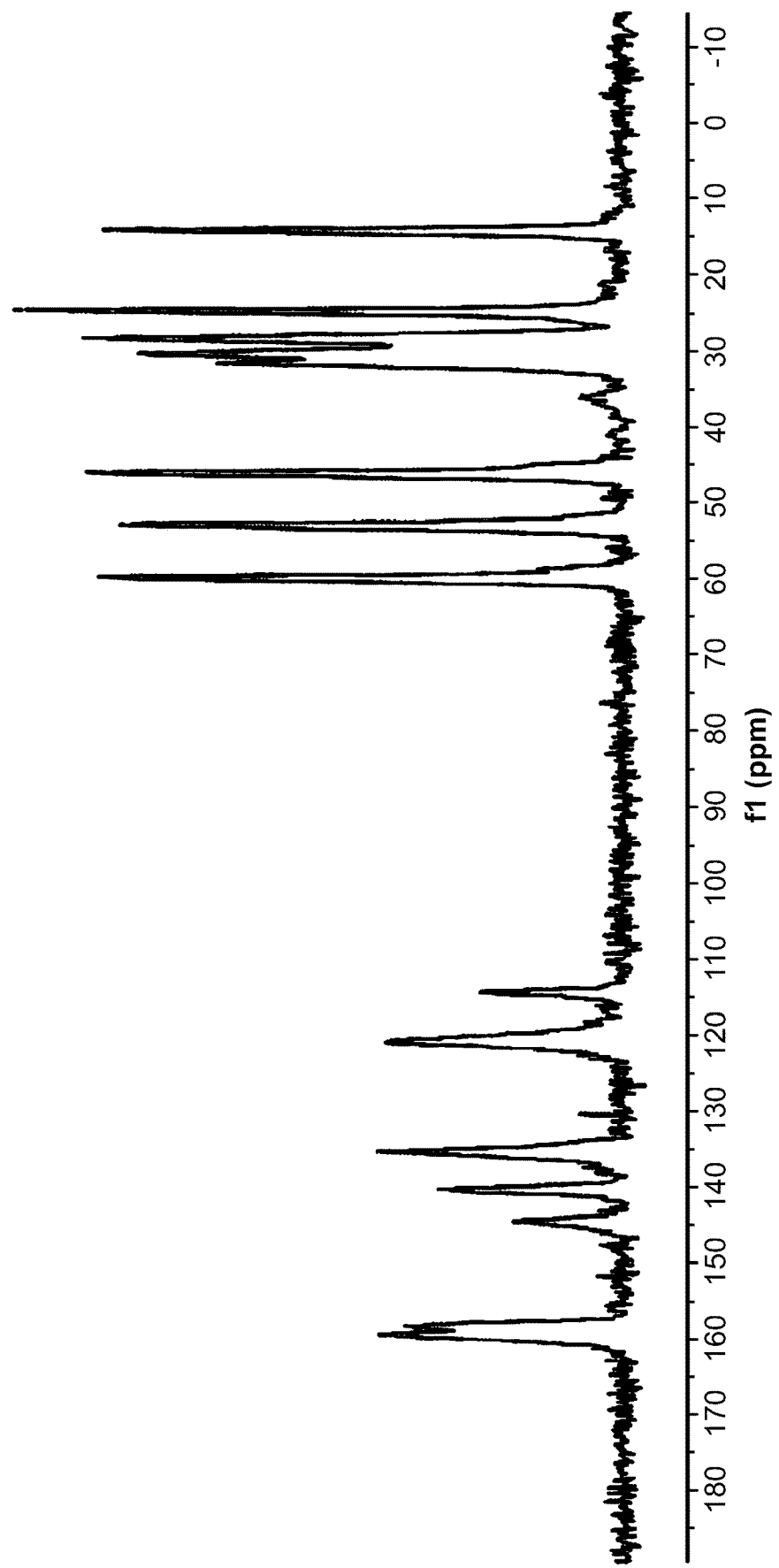
FIG. 4 is a $^{13}$C ssNMR spectrum of Compound 1 Crystalline Form A.
Figure 5:
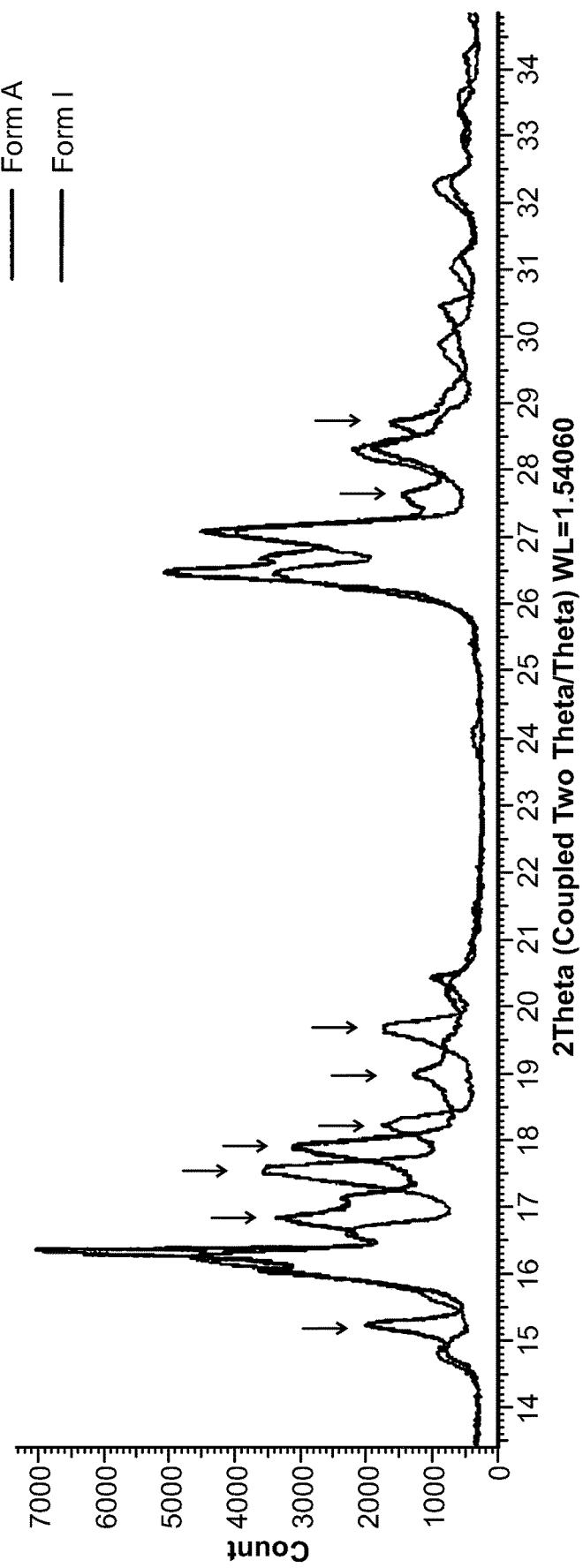
FIG. 5 is an overlay of the XRPD patterns of Compound 1 Crystalline Form 1 and Compound 1 Crystalline Form A.
Figure 6:
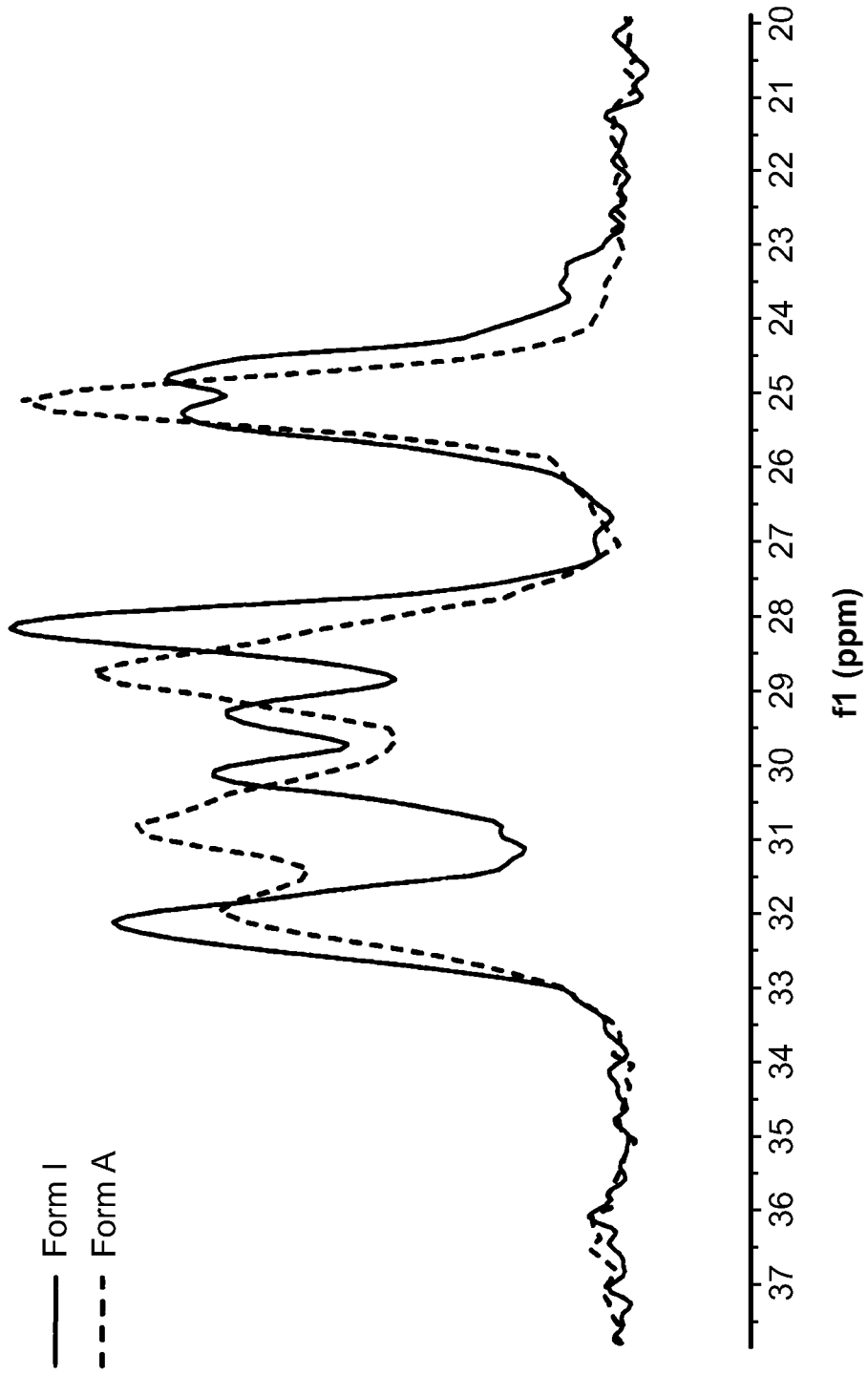
FIG. 6 is an overlay of a portion of the $^{13}$C ssNMR spectra for Compound 1 Crystalline Form 1 and Compound 1 Crystalline Form A.

FIG. 4 shows a $^{13}$C ssNMR spectrum of Compound 1 Crystalline Form A.

In some embodiments, Form A is characterized by a solid-state $^{13}$C NMR pattern including characteristic peaks expressed in ppm at 32.1±0.5, 30.8±0.5, 28.8±0.5, and 25.2±0.5. In some embodiments, Form A is characterized by a solid-state $^{13}$C NMR pattern including characteristic peaks expressed in ppm at 159.7±0.5, 158.5±0.5, 144.8±0.5, 140.6±0.5, 135.6±0.5, 121.0±0.5, 114.6±0.5, 60.3±0.5, 53.4±0.5, 46.6±0.5, 32.1±0.5, 30.8±0.5, 28.8±0.5, 25.2±0.5, and 14.5±0.5.

In some embodiments, Form A is characterized by a solid-state $^{13}$C NMR pattern substantially as depicted in FIG. 4.

FIG. 9 shows an ORTEP figure of the Compound 1 Crystalline Form A crystal structure with hydrogen atoms omitted.

In some embodiments, Form A is characterized by colorless crystals. In some embodiments, Form A is characterized by platelet crystals. In some embodiments, Form A is characterized by a monoclinic crystal system. In some embodiments, Form A is characterized by a C2 (#5) space group. In some embodiments, Form A is characterized by the lattice parameters: a=12.031(2) Å; b=6.2460(8) Å; c=21.947(4) Å; β=95.26(1)°; and V=1642.3(4) Å$^3$. In some other embodiments, Form A is characterized by any of the crystallographic parameters listed in Example 14.

In some embodiments, Form A is characterized by an ORTEP figure with hydrogen atoms omitted substantially as depicted in FIG. 9.

In some embodiments, Form A is characterized by Low frequency Raman spectroscopy including characteristic peaks at 15.6±0.4 cm$^{-1}$.

In some embodiments, the solubility of Form A in water/DMSO at 60° C. is substantially as depicted in FIG. 7.

In some embodiments, Form A is not hygroscopic at 25° C. In some embodiments, Form A is not hygroscopic at 40° C. In some embodiments, Form A is not hygroscopic at temperatures ranging from 25° C. to 40° C.

In some embodiments, Form A is chemically and optically stable at 80° C. (closed environment) for at least eight weeks. In some embodiments, Form A is chemically and optically stable at 60° C./75% relative humidity (open environment) for at least eight weeks.

In some embodiments, crystalline Compound 1 is a mixture of Compound 1 Crystalline Form I and Compound 1 Crystalline Form A.

Methods of Use and Pharmaceutical Compositions

Compound 1 and/or tautomers thereof, and crystalline forms thereof are useful as agents for the prophylaxis or treatment of cancer. Accordingly, Compound 1 can be used for inhibiting excessive or abnormal Cdc7 action in mammals (e.g., mouse, rat, hamster, rabbit, cat, dog, bovine, sheep, monkey, human).

In some embodiments, the present disclosure provides a pharmaceutical composition comprising crystalline 2-[(2S)-1-azabicyclo[2.2.2]oct-2-yl]-6-(3-methyl-1H-pyrazol-4-yl)thieno[3,2-d]pyrimidin-4(3H)-one hemihydrate (Compound 1) and/or tautomers thereof, wherein Compound 1 has the structure:

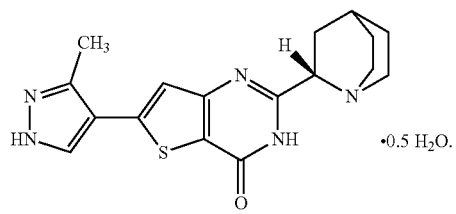 [SMILES: Cc1n[nH]cc1-c1cc2nc([C@@H]3CC4CCN3CC4)[nH]c(=O)c2s1]

In some embodiments, the present disclosure provides a pharmaceutical composition comprising Compound 1 Crystalline Form I. In some embodiments, the present disclosure provides a pharmaceutical composition comprising Compound 1 Crystalline Form A. In some embodiments, the present disclosure provides a pharmaceutical composition comprising a mixture of Compound 1 Crystalline Form I and Compound 1 Crystalline Form A.

In some embodiments, the present disclosure provides a method of inhibiting a cell division cycle 7 in a mammal, which comprises administering an effective amount of a crystalline Compound 1 and/or tautomers thereof or a pharmaceutical composition comprising a crystalline Compound 1 and/or tautomers thereof.

In some embodiments, the present disclosure provides a method for the treatment of cancer in a mammal, wherein said cancer is mediated by cell division cycle 7, which comprises administering an effective amount of a crystalline Compound 1 and/or tautomers thereof or a pharmaceutical composition comprising a crystalline Compound 1 and/or tautomers thereof.

In some embodiments, a crystalline Compound 1 and/or tautomers thereof or a pharmaceutical composition comprising a crystalline Compound 1 and/or tautomers thereof is useful for the treatment of cancer. Non-limiting examples of cancer include colorectal cancer (e.g., colorectal cancer, rectal cancer, anal cancer, familial colorectal cancer, hereditary nonpolyposis colorectal cancer, gastrointestinal stromal tumor), lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophagus cancer, gastric cancer (e.g., papillary adenocarcinoma, mucinous adenocarcinoma, adenosquamous carcinoma), duodenal cancer, small intestinal cancer, breast cancer (e.g., infiltrating intraductal carcinoma, noninfiltrating intraductal carcinoma, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer), liver cancer (e.g., hepatocellular cancer, primary liver cancer, extrahepatic bile duct cancer), thyroid cancer (e.g., medullary thyroid carcinoma), kidney cancer (e.g., renal cell carcinoma, transitional cell carcinoma of renal pelvis and urinary duct), uterine cancer (e.g., cervical cancer, cancer of uterine body, uterus sarcoma), brain tumor (e.g., medulloblastoma, glioma, pineal astrocytoma, pilocytic astrocytoma, diffuse astrocytoma, anaplastic astrocytoma, pituitary adenoma), retinoblastoma, skin cancer (e.g., basal cell tumor, malignant melanoma), sarcoma (e.g., rhabdomyosarcoma, leiomyosarcoma, soft tissue sarcoma), malignant bone tumor, urinary bladder cancer, hematologic cancer (e.g., multiple myeloma, leukemia, malignant lymphoma, Hodgkin's disease, chronic bone marrow proliferative disease), unknown primary cancer], a cancer growth inhibitor, a cancer metastasis suppressive agent, apoptosis promoter, and the like.

In some embodiments, a crystalline Compound 1 and/or tautomers thereof or a pharmaceutical composition comprising a crystalline Compound 1 and/or tautomers thereof is useful for the treatment of hematologic cancer, breast cancer, colorectal cancer, lung cancer, pancreatic cancer, and the like.

A crystalline Compound 1 and/or tautomers thereof or a pharmaceutical composition comprising a crystalline form of Compound 1 and/or tautomers thereof can be administered orally.

In some embodiments, a pharmaceutical composition comprising crystalline Compound 1 and/or tautomers thereof is formulated in an oral dosage form. In some further embodiments, a pharmaceutical composition comprising crystalline Compound 1 and/or tautomers thereof is administered orally.

Examples of an oral dosage form of a pharmaceutical composition of the present disclosure include an oral preparation such as a capsule.

In some embodiments, a pharmaceutical composition comprises Compound 1 Crystalline Form I.

In some embodiments, a pharmaceutical composition comprises Compound 1 Crystalline Form A.

In some embodiments, a pharmaceutical composition comprises Compound 1 Crystalline Form I or Compound 1 Crystalline Form A and further comprises a filler. In some embodiments, said filler is mannitol or lactose. In some embodiments, said filler is present in an amount ranging from 49 to 90 wt % of the pharmaceutical composition.

In some embodiments, a pharmaceutical composition comprises Compound 1 Crystalline Form I or Compound 1 Crystalline Form A and further comprises a glidant. In some embodiments, said glidant is colloidal silicon dioxide. In some embodiments, said glidant is present in an amount ranging from 1 to 4 wt % of the pharmaceutical composition.

In some embodiments, a pharmaceutical composition comprises a mixture of Compound 1 Crystalline Form I and Compound 1 Crystalline Form A.

In some embodiments, a pharmaceutical composition of the present disclosure comprises crystalline Compound 1 and/or tautomers thereof and at least one filler chosen from mannitol and lactose.

In some embodiments, a pharmaceutical composition of the present disclosure comprises crystalline Compound 1 and/or tautomers thereof and mannitol, wherein the mannitol is present in an amount ranging from 49 to 90 wt % of the pharmaceutical composition.

In some embodiments, a pharmaceutical composition of the present disclosure comprises crystalline Compound 1 and/or tautomers thereof and lactose, wherein the lactose is present in an amount ranging from 49 to 90 wt % of the pharmaceutical composition.

In any of the above-mentioned embodiments, the pharmaceutical composition of the present disclosure comprising crystalline Compound 1 and/or tautomers thereof further comprises colloidal silicon dioxide. In some embodiments, the colloidal silicon dioxide is present in an amount ranging from 1 to 4 wt % of the pharmaceutical composition.

In some embodiments, a pharmaceutical composition comprising a crystalline Compound 1 and/or tautomers thereof is in the form of a capsule.

In some embodiments, said capsule further comprises at least one filler and at least one glidant. In some embodiments, said filler is mannitol. In some embodiments, said glidant is colloidal silicon dioxide.

In some embodiments, a pharmaceutical composition comprising crystalline Compound 1 and/or tautomers thereof in the form of a capsule comprises from 5 to 15 wt % crystalline form of Compound 1 and/or tautomers thereof, from 85 to 95 wt % filler, and from 0.5 to 2% glidant relative to the weight of the capsule, excluding the capsule shell. In some embodiments, the filler is mannitol. In some embodiments, the glidant is colloidal silicon dioxide. In some embodiments, the capsule shell comprises from 20 to 30 wt % relative to the total weight of the capsule.

In some embodiments, the crystalline form is Compound 1 Crystalline Form I. In some embodiments, the crystalline form is Compound 1 Crystalline Form A. In some embodiments, the crystalline form is a mixture of Compound 1 Crystalline Form A and Compound 1 Crystalline Form I.

While the amount of a crystalline Compound 1 and/or tautomers thereof in a pharmaceutical composition of the present disclosure varies depending on the form of the pharmaceutical composition, it is generally present in an amount ranging from 0.01 to 99.9 wt %, for example 2 to 85 wt %, such as 5 to 70 wt %, relative to the weight of the entire pharmaceutical composition.

While the amount of the additive in a pharmaceutical composition of the present disclosure varies depending on the form of the pharmaceutical composition, it is generally present in an amount ranging from 1 to 99.9 wt %, for instance 10 to 90 wt %, relative to the weight of the entire pharmaceutical composition.

The crystalline forms of the present disclosure are stable and have low toxicity, and can be used safely. While the daily dose varies depending on the condition and body weight of the mammal, administration route and the like, in the case of, for example, a crystalline form of the disclosure can be administered orally in the form of a pharmaceutical composition described herein to a mammal for the treatment of cancer. In some embodiments, the dose administered to an adult (body weight about 60 kg) is 30 mg orally once or twice a day.

General Synthetic Methods

The discovery of methods to prepare the crystalline forms described herein was particularly challenging due to the close relative solubilities of the crystalline forms. Indeed, the development of robust and consistent manufacturing processes of the disclosure required a thorough understanding of the compounds' crystallization behavior and associated thermodynamics. In one aspect, Compound 1 Crystalline Form I is obtained by a method comprising the step of recrystallizing a crude preparation of Compound 1 and/or tautomers thereof from a mixture comprising DMSO and at least one other solvent chosen from water, acetonitrile and acetone.

In some embodiments, the mixture comprises DMSO and water. In some embodiments, the mixture comprises a volume ratio of 10:1 to 12:1 DMSO:water. In some embodiments, the DMSO is present in an amount ranging from 9.6 to 10.6 mL DMSO/g Compound 1. In some embodiments, the concentration of water ranges from 0 to 8 wt % relative to the total amount of DMSO and water.

In some embodiments, the mixture comprises DMSO and acetone. In some embodiments, the mixture comprises a volume ratio of 10:1 DMSO:acetone. In some embodiments, the mixture comprises DMSO, acetone, and water. In some embodiments, the mixture comprises a volume ratio of 2.4:1:1 DMSO:acetone:water.

In another aspect, Compound 1 Crystalline Form I is obtained by a method comprising slurrying Compound 1 Crystalline Form A, or a mixture of Compound 1 Crystalline Form A with Compound 1 Crystalline Form I, in a mixture comprising DMSO and water.

In some embodiments, the slurry is stirred at about 300 rpm. In some embodiments, the slurry is heated to a temperature ranging from 55° C. to 65° C. In some embodiments, the slurry is stirred for about a period of time ranging from 12 to 26 hours. In some embodiments, the slurry comprising Compound 1 Crystalline Form A and a mixture comprising DMSO and water is circulated through a wet mill.

In another aspect of the present disclosure, Compound 1 Crystalline Form A is obtained by a method comprising the step of recrystallizing a crude preparation of Compound 1 from a mixture comprising DMSO, ethanol, and water.

In some embodiments, the mixture comprises a volume ratio of 1.6:1:3.5 DMSO:ethanol:water.

In another aspect, Compound 1 Crystalline Form A is obtained by a method comprising the step of recrystallizing a crude preparation of Compound 1 from a solution comprising at least one solvent selected from methanol, ethanol, isopropyl alcohol, acetone, ethyl acetate, acetonitrile, or toluene.

In another aspect, Compound 1 Crystalline Form A is obtained by a method comprising the step of recrystallizing a crude preparation of Compound 1 from a mixture comprising water and at least one solvent selected from methanol, ethanol, isopropyl alcohol, tetrahydrofuran, and trifluoroethanol.

In another aspect, Compound 1 Crystalline Form A is obtained by a method comprising the step of recrystallizing a crude preparation of Compound 1 from a mixture comprising water and ethanol.

In another aspect, Compound 1 Crystalline Form A is obtained by a method comprising the step of recrystallizing a crude preparation of Compound 1 from a mixture comprising heptane and at least one solvent selected from methanol, ethanol, isopropyl alcohol, or butan-2-one.

In another aspect, Compound 1 Crystalline Form A is obtained by a method comprising the step of recrystallizing a crude preparation of Compound 1 from a mixture comprising diisopropyl ether and at least one solvent selected from methanol, ethanol, isopropyl alcohol, or butan-2-one.

In another aspect, the present disclosure provides a process for preparing the compound of any one of several embodiments disclosed herein, wherein the process comprises:

(i) (A1-1a) mixing Compound 1 in DMSO to form a solution and heating the solution to a temperature ranging from 50° C. to 60° C.;

(ii) (A1-1b) optionally filtering the solution;

(iii) (A1-2) adding water preheated to a temperature ranging from 50° C. to 60° C. to the solution to form a mixture while maintaining an internal temperature of the mixture ranging from 50° C. to 60° C.;

(iv) (A1-3) seeding the mixture from Step (A1-2) with seed of Compound 1 Crystalline Form I to form a first seeded mixture;

(v) (A1-4) adding water preheated to a temperature ranging from 50° C. to 60° C. to the first seeded mixture to form a second seeded mixture, while maintaining an internal temperature of the second seeded mixture ranging from 50° C. to 60° C. and stirring the second seeded mixture at a temperature ranging from 50° C. to 60° C.;

(vi) (A1-4) ageing the second seeded mixture resulting from Step (A1-4) to provide the Compound 1 Crystalline Form I.

In some embodiments, the total amount of solvent present in any one of steps (A1-1a) to (A1-4) ranges from 9.6 to 10.6 mL solvent/g Compound 1, wherein the solvent comprises DMSO and water.

In some embodiments, the concentration of the water present in any one of steps (A1-1a) to (A1-4) ranges from 0 to 8 wt % relative to the total amount of water and DMSO.

In some embodiments, the concentration of the water in step (A1-3) ranges from 3.5 to 4.3 wt % relative to the total amount of water and DMSO.

In some embodiments, the particle size distribution for the seed crystals of step (A1-3) is characterized by a D10 ranging from 2 to 6 μm, D50 ranging from 9 to 32 μm, or D90 ranging from 32 to 62 μm.

In some embodiments, the amount of seed crystals added in step (A1-3) ranges from 0.5 to 1.0 wt % relative to the total amount of Compound 1.

EXAMPLES

Abbreviations

DMF dimethylformamide
DSC differential scanning calorimetry
DMSO dimethyl sulfoxide
EtOAc ethyl acetate
EtOH ethanol
IPE isopropyl ether
MeOH methanol
MEK methyl ethyl ketone
THF tetrahydrofuran
TMS tetramethylsilane
HRMS high resolution mass spectrum
% ee enantiomeric excess %
hr hour
min minute
m/z mass to charge
MS mass spectrum
NMR nuclear magnetic resonance
RP LC-MS reverse phase liquid chromatography-mass spectrometry
RT room temperature
XRPD X-ray powder diffraction
s singlet
t triplet
m multiplet
br broad
J coupling constant
rpm revolutions per minute
% Weight percent (unless otherwise specified)

Herein, butan-2-one is also referred as methyl ethyl ketone (abbreviated as MEK).

In the following Examples, the ratios shown for mixed solvent systems are volume ratios unless otherwise specified. In addition, % denotes wt % unless otherwise specified.

General Methods

Proton Nuclear Magnetic Resonance ($^1$H-NMR). Proton ($^1$H) nuclear magnetic resonance spectra were obtained on a Varian Mercury 300 spectrometer in DMSO-$d_6$ at 600 MHz.

Solid State Carbon-13 Nuclear Magnetic Resonance ($^{13}$C ssNMR). Solid state carbon-13($^{13}$C) nuclear magnetic resonance spectra were recorded on a Bruker Avance III 500 MHz spectrometer equipped with a 4 mm H-F/X double resonance probe CPMAS probe. The spectra were collected utilizing proton/carbon-13 cross-polarization at 12.5 kHz with a contact time of 700 ms, a relaxation delay of 10 s, and a SPINAL64 decoupling of 100 kHz. A line broadening of 10 Hz was applied to the spectrum before Fourier Transformation. TMS was used as the internal standard for calibrating chemical shifts. Chemical shifts are reported on the TMS scale using the carbonyl carbon of glycine (176.70 ppm) as a secondary reference.

X-ray Powder Diffraction (XRPD). X-ray powder diffraction (XRPD) patterns were collected using a Bruker AXS D8 Advance X-ray Diffractometer with Cu Kα radiation at 40 kV and 40 mA. Approximately 100 mg sample was gently flattened at the center of a 50 mm diameter VeroWhitePlus sample holder for powder diffraction analysis. The sample was run as a continuous scan from 2.9° to 35° 2θ using 2θ/θ locked coupled angles with step size of 0.025° 2θ and data collection time of 0.4 seconds per step. The sample run was carried out under ambient conditions, and all data analysis was performed using EVA version 9.0 software.

In some experiments, X-ray powder diffraction patterns were collected using a Rigaku Ultima IV (Rigaku, Tokyo, Japan) with Cu-Kα radiation generated at 50 mA and 40 kV. A sample was placed on a silicon plate at room temperature. Data were collected from 2° to 35° (2θ) at a step size of 0.02° and a scanning speed of 6°/min.

Water content. Water content was determined using a Karl Fischer moisture meter (Hiranuma Moisture Meter AQ-7, product of Hiranuma Sangyo Co., Ltd.)

Single crystal X-ray diffraction. X-ray diffraction data were recorded on a Rigaku R-AXIS RAPID (Rigaku, Tokyo, Japan) with graphite-monochromated Cu-Kα radiation. The data collection was conducted at 25° C. The crystal structures were solved via direct methods and refined using a full-matrix least-squares procedure. The nonhydrogen atoms were refined anisotropically, and the hydrogen atoms were located geometrically and refined using a riding model. All calculations were performed using the Crystal Structure crystallographic software package (Rigaku, Tokyo, Japan), except for the direct solution and refinement calculations, which were performed using SHELXL-97. Packing diagrams were generated using Mercury.

Raman Spectroscopy. Low frequency Raman spectra were collected using a RXN1 systems and an air-cooled CCD detector (Kaiser Optical Systems, Inc., Ann Arbor, Mich., USA) equipped with a SureBlock TRUMICRO module (Ondax Inc., Monrovia, Calif. USA) with a 976 nm excitation laser. Data was collected using a 10-fold objective lens with 10 seconds exposure. The Raman shift was calibrated using sulfur.

Example 1. Recrystallization of Compound 1 Crystalline Form A from Various Solutions Recrystallization of Compound 1 Crystalline Form A was investigated in various solvent conditions. As shown in Table 1, Compound 1 Crystalline Form A was dissolved in 12 solvents. One of water, heptane or IPE was added as an anti-solvent to maintain the saturation state. Recrystallization in heptane yielded a sufficient amount of solids for analysis after gradual cooling. XRPD and TGA/DSC analysis indicated that solids obtained from MEK or THF/IPE were amorphous (Table 1). Crystals obtained from THF, trifluoroethanol, THF/heptane, chloroform/heptane, chloroform/IPE and trifluoroethanol/IPE were characterized as solvates by XRPD and TGA/DSC analysis. Crystals obtained from all other solvents were confirmed to be Compound 1 Crystalline Form A based on XRPD analysis.

X-ray powder diffraction patterns were collected using a Rigaku Ultima IV (Rigaku, Tokyo, Japan) with Cu-Kα radiation generated at 50 mA and 40 kV. A sample was placed on a silicon plate at room temperature. Data were collected from 2° to 35° (2θ) at a step size of 0.02° and a scanning speed of 6°/min.

TABLE 1

Summary of Recrystallization Study

| | Estimated solubility at 55° C. (mg/mL) | Crystal form | | |
|---|---|---|---|---|
| | | No additive | Antisolvent | | |
| | | | Water | Heptane | IPE |
| Methanol | 33.3 | Form A | Form A | | Form A |
| Ethanol | 10.5 | Form A | Form A | Form A | Form A |
| IPA | 6.7 | Form A | Form A | Form A | Form A |
| Acetone | <2 | Form A | —[a] | —[a] | —[a] |
| MEK | 2.9 | Amorphous | | Form A | Form A |
| Ethyl acetate | <2 | Form A | | —[a] | —[a] |
| Acetonitrile | <2 | Form A | —[a] | | —[a] |
| Toluene | <2 | Form A | | —[a] | —[a] |
| Formamide | 10.0 | —[b] | —[b] | | |
| Chloroform | 2.8 | —[c] | | Solvate | Solvate |
| THF | 9.1 | Solvate | Form A | Solvate | Amorphous |
| Trifluoro-ethanol | >100 | Solvate | Form A | | Solvate |

[a]Not performed because of low solubility, [b]Not obtained after slow cooling, [c]Paste-like residue.

Example 2. Preparation of Compound 1 Crystalline Form A Using DMSO/Ethanol/Water Crude Compound 1 was obtained according to the method described in Example 178 U.S. Pat. No. 8,722,660 B2. Crude Compound 1 (300 g) was suspended in DMSO (1560 mL) and ethanol (930 mL). The suspension then was dissolved by heating to 75° C. to 85° C. After confirmation of dissolution, dust removal filtration was carried out, and the residue was washed with a mixed solution of DMSO (1040 mL) and ethanol (620 mL). The filtrate and washing solution after the dust removal filtration were combined and stirred at 75° C. to 85° C. After confirmation of no precipitation, water (5580 mL) was added dropwise for 1 hr or longer at the same temperature. After dropwise addition, the mixture was stirred at the same temperature for 1 hr or longer. After confirmation of the precipitation of the crystals, the mixture was allowed to cool to 20° C. to 30° C. and stirred for 2 hrs or longer. After stirring, the crystals were collected by filtration and washed with water (3000 mL) and acetone (1500 mL) successively to give wet crystals. The obtained wet crystals were dried under reduced pressure at 60° C. to give Compound 1 as crystals (Compound 1 Crystalline Form A, 207.3 g, yield 69.1%). The obtained Compound 1 Crystalline Form A crystals (193.3 g) were pulverized in a Jet Mill to give a crystalline powder (pulverized product, form A crystal, 188.9 g). The obtained crystals contained 2.5% water and were characterized by a XRPD pattern with specific peaks at d values (or d-spacings) of 21.5, 10.9, 7.3, 5.4, 5.0, 4.9, 4.5, 3.7, 3.4, 3.3 and 3.0 Å.

$^1$H-NMR (600 MHz, DMSO-$d_6$) δ 1.39-1.48 (m, 2H), 1.48-1.58 (m, 2H), 1.75 (t, J=11.1 Hz, 1H), 1.87 (br s, 1H), 2.24-2.36 (m, 1H), 2.46 (s, 3H), 2.53-2.65 (m, 2H), 2.80-2.97 (m, 1H), 3.07 (t, J=11.3 Hz, 1H), 3.91 (t, J=8.9 Hz, 1H), 7.44 (s, 1H), 8.04 (br s, 1H).

Analytical Calculated for $C_{17}H_{20}N_5O_{1.5}S$: C, 58.27; H, 5.75; N, 19.98; O, 6.85; S, 9.15. Experimental: C, 58.22; H, 5.80; N, 20.03; S, 9.09.

X-ray powder diffraction patterns were collected using a Rigaku Ultima IV (Rigaku, Tokyo, Japan) with Cu-Kα radiation generated at 50 mA and 40 kV. A sample was placed on a silicon plate at room temperature. Data were collected from 2° to 35° (2θ) at a step size of 0.02° and a scanning speed of 6°/min.

Example 3. Preparation of Compound 1 Crystalline Form I Using DMSO/Acetone

Crude Compound 1 was obtained according to the method described in Example 178 of U.S. Pat. No. 8,722,660 B2. Crude Compound 1 (35 g) was suspended in DMSO (105 mL). The suspension was then dissolved by heating to 70° C. to 80° C. After confirmation of dissolution, dust removal filtration was carried out, and the residue was washed with DMSO (70 mL). The filtrate and washing solution after the dust removal filtration were combined and stirred at 70° C. to 80° C. After confirmation of no precipitation, the mixture was allowed to cool to 50° C. to 60° C. After cooling, acetone (1750 mL) was added dropwise for 1 hr or longer at the same temperature. After dropwise addition, the mixture was stirred at the same temperature for 1 hr or longer. After confirmation of the precipitation of the crystals, the mixture was allowed to cool to 20° C. to 30° C. and stirred for 1 hr or longer. After stirring, the crystals were collected by filtration and washed with acetone (350 mL) to give wet crystals. The obtained wet crystals were dried under reduced pressure at 60° C. to give Compound 1 as crystals (Compound 1 Crystalline Form I, 26.5 g, yield 75.7%). The obtained Compound 1 Crystalline Form I crystals (21.5 g) were pulverized in a Jet Mill to give a crystalline powder (pulverized product, form I crystal, 18.2 g). The obtained crystals contained 2.6% of water and characterized by a XRPD pattern with specific peaks at d values (or d-spacings) of 21.6, 10.9, 7.2, 5.8, 5.4, 5.0, 4.3, 3.4, 3.3, 3.2 and 2.9 Å.

$^1$H-NMR (600 MHz, DMSO-$d_6$) δ 1.39-1.48 (m, 2H), 1.48-1.59 (m, 2H), 1.75 (t, J=11.1 Hz, 1H), 1.87 (br s, 1H), 2.25-2.36 (m, 1H), 2.46 (s, 3H), 2.53-2.65 (m, 2H), 2.81-2.97 (m, 1H), 3.07 (t, J=11.3 Hz, 1H), 3.91 (t, J=8.9 Hz, 1H), 7.44 (s, 1H), 8.04 (br s, 1H).

Analytical Calculated for $C_{17}H_{20}N_5O_{1.5}S$: C, 58.27; H, 5.75; N, 19.98; O, 6.85; S, 9.15. Experimental: C, 58.22; H, 5.73; N, 19.84; S, 9.12.

X-ray powder diffraction patterns were collected using a Rigaku Ultima IV (Rigaku, Tokyo, Japan) with Cu-Kα radiation generated at 50 mA and 40 kV. A sample was placed on a silicon plate at room temperature. Data were collected from 2° to 35° (2θ) at a step size of 0.02° and a scanning speed of 6°/min.

Example 3-2. Preparation of Compound 1 Crystalline Form I Using DMSO/Acetonitrile Crude Compound 1 was obtained according to the method described in Example 178 of U.S. Pat. No. 8,722,660 B2. Crude Compound 1 (1 g) was suspended in DMSO (5 mL). The suspension was then dissolved by heating to 75° C. to 80° C. After confirmation of dissolution, acetonitrile (50 mL) was added dropwise for 1 hr or longer at the same temperature. The mixture was allowed to cool to 60° C. to 70° C. and the mixture was stirred at the same temperature for 1 hr or longer. After confirmation of the precipitation of the crystals, the mixture was allowed to cool to 20° C. to 30° C. and stirred for 1 hr or longer. After stirring, the crystals were collected by filtration and washed with acetonitrile (10 mL) to give wet crystals. The obtained wet crystals were dried under reduced pressure at 60° C. to give Compound 1 as crystals (Compound 1 Crystalline Form I, 862 mg, yield 86.2%).

Example 3-3. Preparation of Compound 1 Crystalline Form A Using Ethanol/Water

Crude Compound 1 was obtained according to the method described in Example 178 U.S. Pat. No. 8,722,660 B2. Crude Compound 1 (9.53 g) was suspended in a solution of ethanol and water (100/1, v/v, 400 mL). The suspension then was heated to 75° C. to 85° C. A solution of ethanol-water (100/1, v/v, 380 mL) was added slowly at same temperature to give a solution. The solution was allowed to cool to 20° C. to 30° C. and stirred for 16 h. The crystals were collected by filtration and washed with ethanol (60 mL) to give Compound 1 as crystals (Compound 1 Crystalline Form A, 7.73 g, yield 81.1%). The obtained crystals contained 2.6% water and were characterized by a XRPD pattern with specific peaks at d values (or d-spacings) of 22.1, 11.0, 7.3, 5.5, 5.1, 4.9, 4.5, 3.7, 3.4, 3.3 and 3.0 Å.

$^1$H-NMR (300 MHz, DMSO-$d_6$) δ 1.37-1.61 (m, 4H), 1.69-1.91 (m, 2H), 2.23-2.33 (m, 1H), 2.46 (s, 3H), 2.54-2.67 (m, 2H), 2.77-2.94 (m, 1H), 3.00-3.14 (m, 1H), 3.91 (t, J=8.9 Hz, 1H), 7.44 (s, 1H), 8.03 (br s, 1H), 12.24 (br s, 1H).

Analytical Calculated for $C_{17}H_{20}N_5O_{1.5}S$: C, 58.26; H, 5.75; N, 19.98. Experimental: C, 58.09; H, 5.69; N, 19.84.

Example 4. Preparation of Compound 1 Crystalline Form I Using DMSO/Acetone/Water Crude Compound 1 was obtained according to the method described in Example 178 of U.S. Pat. No. 8,722,660 B2. Crude Compound 1 (30 g) was dissolved in DMSO (300 mL) at 20° C. to 30° C. After confirmation of dissolution, dust removal filtration was carried out and a filtrate solution was obtained. The residue was washed with DMSO (60 mL), and a washing solution was obtained. A mixed solution of acetone (150 mL) and water (150 mL) was stirred at 45° C. to 55° C., and 45 mL of the filtrate solution was added dropwise for 10 to 30 min at the same temperature. After dropwise addition, the mixture was stirred at the same temperature for 10 min. To the mixture, 15 mL of the filtrate solution was added dropwise for 3 to 10 min at the same temperature. After dropwise addition, the mixture was stirred at the same temperature for 1 hr or longer. After confirmation of the precipitation of the crystals, the rest of the filtrate solution was added dropwise for 1 to 2 hr at the same temperature. After dropwise addition, the washing solution was added dropwise at the same temperature. After dropwise addition, the mixture was stirred at the same temperature for 1 hr. After stirring, the mixture was allowed to cool to 20° C. to 30° C. and stirred for 1 hr or longer. After stirring, the crystals were collected by filtration and washed with water (150 mL) and acetone (150 mL) successively to give wet crystals. The obtained wet crystals were dried under reduced pressure at 60° C. to give Compound 1 as crystals (Compound 1 Crystalline Form I, 25.9 g, yield 86.3%).

Example 5. Slurry Conversion of Compound 1 Crystalline Form A/I to Compound 1 Crystalline Form I A mixture of Compound 1 Crystalline Form A and Compound 1 Crystalline Form I, herein referred to as Compound 1 Crystalline Form A/I (5 g) was suspended in a mixture of DMSO (60 mL) and water (5.15 mL). Then, the suspension was heated to 55° C. to 65° C. and stirred for 12 hr or longer. Thereafter, a part of the solids was collected by filtration. As a result of XRPD measurements, Compound 1 Crystalline Form A/I was confirmed to convert to Compound 1 Crystalline Form I. After confirmation of the conversion, the mixture was allowed to cool to 20° C. to 30° C. over 3 hrs and stirred at the same temperature for 1 hr or longer. Thereafter, a part of the solids was collected by filtration. As a result of XRPD measurements, the identification of the crystals as Compound 1 Crystalline Form I was confirmed. After confirmation, a mixture of acetone (25 mL) and water (25 mL) was added dropwise for 30 min or longer at 20° C. to 30° C. After dropwise addition, the mixture was stirred at the same temperature for 1 hr or longer. After stirring, the crystals were collected by filtration and washed with water (25 mL) and acetone (25 mL) successively to give wet crystals. The obtained wet crystals were dried under reduced pressure at 60° C. to give Compound 1 as crystals (Compound 1 Crystalline Form I, 4.7 g, yield 94.0%).

X-ray powder diffraction patterns were collected using a Rigaku Ultima IV (Rigaku, Tokyo, Japan) with Cu-Kα radiation generated at 50 mA and 40 kV. A sample was placed on a silicon plate at room temperature. Data were collected from 2° to 35° (2θ) at a step size of 0.02° and a scanning speed of 6°/min.

Example 6. Compound 1 Crystal Forms at Various Concentrations and Water Contents To study the effects of (i) concentration of Compound 1 and (ii) water content on the crystalline form of Compound 1, the following screen was performed.

Compound 1 Crystalline Form A was completely dissolved in 5 mL DMSO/g Compound 1 Crystalline Form A at 80° C. and filtered through a 0.22 μm pore membrane filter. Then, part of the resulting solution was diluted by 4/3, 2 or 3-fold with DMSO. The Compound 1 solutions were added into acetone containing various percentage of water at 55° C. The solutions were incubated at 55° C. for 1 hr and stirred at 300 rpm while cooling to 25° C. at 3° C./hr. The precipitate was harvested from each solution, and crystal form of the precipitates was studied by XRPD analysis. X-ray powder diffraction patterns were collected using a Rigaku Ultima IV (Rigaku, Tokyo, Japan) with Cu-Kα radiation generated at 50 mA and 40 kV. A sample was placed on a silicon plate at room temperature. Data were collected from 2° to 35° (2θ) at a step size of 0.02° and a scanning speed of 6°/min. The results are shown in Table 2.

TABLE 2

Crystal forms at various concentrations and water contents

| Final concentration (g/L) | Water content in acetone before the DMSO solution addition (% v/v) | | | | | | | | | | | | | | | |
|---|---|---|---|---|---|---|---|---|---|---|---|---|---|---|---|---|
| | 0 | 0.1 | 0.2 | 0.3 | 0.5 | 0.7 | 1.0 | 1.5 | 2 | 3 | 5 | 7 | 10 | 20 | 30 | 50 |
| 18.2 | I | I | I | I | I | A+I | A+I | A | A | A | A | A | A | A | A | A+I |
| 13.6 | S | I | I | I | I | I | I | A+I | A+I | A+I | A+I | A+I | I | I | I | I |
| 9.1 | S | I | I | I | I | I | I | I | I | I | I | I | I | I | I | I |
| 6.1 | S | S | S | S | I | I | I | I | I | I | I | I | I | I | I | S |

A: Compound 1 Crystalline Form A crystal was obtained.
I: Compound 1 Crystalline Form I crystal was obtained.
A + I: A mixture of Compound 1 Crystalline Form A and Compound 1 Crystalline Form I was obtained
S: No solid precipitated.

This result demonstrated that, at high concentrations of Compound 1 (i.e., 18.2 g/L), pure Compound 1 Crystalline Form I will not crystallize unless the water content in acetone before the DMSO solution addition is low (i.e, less than 0.7% v/v).

Suitable water content for further optimization studies to obtain Compound 1 Crystalline Form I was determined based on the screening results. Then, Compound 1 in DMSO solution (10 mL DMSO/g Compound 1) was added dropwise to a mixture of acetone and water (10 mL acetone/water per g Compound 1) at 50° C. with various addition speeds. Based on the results, which are shown in Table 3 below, the addition speed of Compound 1 in DMSO solution should be slow throughout the addition in order to obtain Compound 1 Crystalline Form I. Under these conditions, fast addition favored formation of Compound 1 Crystalline Form A.

TABLE 3

Crystal forms of Compound 1 obtained using various addition procedures

| Addition procedure | Water content in acetone (% v/v) | Crystal form | Yield |
|---|---|---|---|
| Add: 10 min | 20 | Form A | 82.4% |
| Add: 60 min | 20 | Form A | 80.9% |
| 1. Add 1 vol: 10 min<br>2. Stir: 1 h<br>3. Add 9 vol: 10 min | 20 | Form A/I* | 77.8% |
| 1. Add 1 vol: 10 min<br>2. Stir: 1 h<br>3. Add 9 vol: 65 min | 20 | Form I | 79.2% |
| 1. Add 1.5 vol: 15 min<br>2. Stir: 1 h<br>3. Add 8.5 vol: 60 min | 50 | Form I | 90.2% |

*Form A/I denotes a mixture of Compound 1 Crystalline Form I and Compound 1 Crystalline Form A Example 7. Solubility of Compound 1 Crystalline Form I and Compound 1 Crystalline Form A in 200 mM Phosphate Buffer (pH 6.8)

About 2 mg of Compound 1 Crystalline Form A made in example 2 or Compound 1 Crystalline Form I made in example 3-2 and 2 mL of 200 mM phosphate buffer (pH 6.8) were added into a glass test tube. The test tube was shaken vigorously and incubated at 10° C., 20° C., 30° C. or 40° C. for 20 hrs. After the incubation, the suspension was centrifuged and the supernatant was filtered through a 0.22 μm pore membrane filter. The filtrate solutions were diluted 2-fold with 50 mM sodium perchlorate buffer (pH 2.5)/acetonitrile (1/1, v/v). Concentration was determined by HPLC. The results are shown in Table 4.

TABLE 4

Solubility of Compound 1 Crystalline Form I and Compound 1 Crystalline Form A in 200 mM phosphate buffer (pH 6.8).

| Temperature (° C.) | Solubility (μg/mL) | | | |
|---|---|---|---|---|
| | 10 | 20 | 30 | 40 |
| Form A | 102 | 104 | 115 | 136 |
| Form I | 63 | 71 | 80 | 99 |

Example 8. Recrystallization of Compound 1 Crystalline Form I

Compound 1 crystalline form I (9.5 kg, 97.1% ee) was dissolved in DMSO (85.5 L, 9.0 mL DMSO/g Compound 1). The solution was heated to 60° C. The reaction mixture was polish filtered while maintaining a mixture temperature of approximately 60° C. The transfer lines were rinsed with DMSO (6.7 L, 0.7 mL DMSO/g Compound 1). The Compound 1 solution and the rinse solution were combined. The Compound 1 solution was then heated to 60° C. Preheated 60° C. water (4.0 L, 0.43 mL water/g Compound 1) was added to the Compound 1 solution over 1 hr while maintaining an internal temperature of 60° C. Compound 1 Crystalline Form I (106.0 g, 1.1 weight %) seed crystals were charged to the reaction mixture. The reaction mixture was stirred at 60° C. for 1 hr. Preheated 60° C. water (3.9 L, 0.41 mL water/g Compound 1) was added to the Compound 1 suspension over 3 hrs while maintaining a batch temperature of 60° C. Upon completion of water addition, the slurry was stirred at 60° C. for a minimum of 4.5 hrs. A sample was taken from the slurry and filtered to obtain crystals. The crystals were analyzed by XRPD. If the sample crystals were not all Compound 1 Crystalline Form I, the stirring was continued. Samples were taken then analyzed every 6 hrs until Compound 1 Crystalline Form A was not detected by XRPD in the sample crystals. The reaction was cooled to 25° C. in 5 hrs. The solids were filtered and washed with 3 mL of 2:1/acetone:water (28.5 L) per g of solid twice. The solids were dried under vacuum at 60° C. for 18 hrs to afford 7.3 kg (76.8% yield) of the desired product. The desired product was obtained as a white solid. HPLC showed the obtained product was >99% purity and chiral HPLC showed 99.1% ee. Analysis by XRPD confirmed the obtained product was Compound 1 Crystalline Form I.

X-ray powder diffraction (XRPD) patterns were collected using a Bruker AXS D8 Advance X-ray Diffractometer with Cu Kα radiation at 40 kV and 40 mA. Approximately 100 mg sample was gently flattened at the center of a 50 mm diameter VeroWhitePlus sample holder for powder diffraction analysis. The sample was run as a continuous scan from 2.9° to 35° 2θ using 2θ/θ locked coupled angles with step size of 0.025° 2θ and data collection time of 0.4 seconds per step. The sample run was carried out under ambient conditions, and all data analysis was performed using EVA version 9.0 software.

Example 9. Slurry Conversion of Compound 1 Crystalline Form A/I to Obtain Compound 1 Crystalline Form I DMSO (240 mL, 3380 mmol, 12 mL DMSO/g Compound 1 Crystalline Form A/I) and water (20.6 mL, 1140 mmol, 1 mL water/g Compound 1 Crystalline Form A/I) were added to a 500 mL OptiMax reactor. Compound 1 Crystalline Form A/I (20.00 g, 58.58 mmol) was then added to the reactor. The resulting slurry was stirred at 300 rpm and heated to 60° C. After stirring for 26 hrs, a sample of the slurry was removed, filtered hot, and washed with a minimal amount of 1:1 acetone:water to yield approximately 100 mg of solids, which were submitted for XRPD analysis and found to be Compound 1 Crystalline Form I. The bulk slurry was cooled to 22° C. over 6 hrs and was stirred at 22° C. overnight. In the morning, the slurry was filtered and washed twice with 60 mL of 2:1 acetone:water. The filter cake was dried over 72 hrs at 45° C. under vacuum. XRPD of the bulk dried solid showed that it was Compound 1 Crystalline Form I.

X-ray powder diffraction (XRPD) patterns were collected using a Bruker AXS D8 Advance X-ray Diffractometer with Cu Kα radiation at 40 kV and 40 mA. Approximately 100 mg sample was gently flattened at the center of a 50 mm diameter VeroWhitePlus sample holder for powder diffraction analysis. The sample was run as a continuous scan from 2.9° to 35° 2θ using 2θ/θ locked coupled angles with step size of 0.025° 2θ and data collection time of 0.4 seconds per step. The sample run was carried out under ambient conditions, and all data analysis was performed using EVA version 9.0 software.

Example 10. Slurry Conversion of Compound 1 Crystalline Form A/I with Wet Milling to Obtain Compound 1 Crystalline Form I DMSO (240 mL, 3380 mmol, 12 mL DMSO/g Compound 1 Crystalline Form A/I) and water (20.6 mL, 1140 mmol, 1 mL water/g Compound 1 Crystalline Form A/I) were added to a 500 mL OptiMax reactor attached to a recirculating IKA lab-scale rotor-stator wet mill. Compound 1 Crystalline Form A/I (20.00 g, 58.58 mmol) was then added to the reactor. The resulting slurry was circulated through the wet mill (set at 10,000 rpm) for 1 min. The slurry was then passed once through the wet mill and transferred back to the OptiMax reactor. The slurry was then heated to 60° C. After stirring for 17.5 hrs at 60° C., a sample of the slurry was removed, filtered hot, and washed with a minimal amount of 1:1 acetone:water to yield approximately 100 mg of solids, which were submitted for XRPD analysis and found to be Compound 1 Crystalline Form I. The slurry was cooled to 22° C. over 6 h and stirred at 22° C. overnight. In the morning, the slurry was filtered and washed twice with 60 mL of 2:1 acetone:water. The filter cake was dried over 72 hrs at 45° C. under vacuum. XRPD analysis of the bulk dried solid showed that it was Compound 1 Crystalline Form I.

X-ray powder diffraction (XRPD) patterns were collected using a Bruker AXS D8 Advance X-ray Diffractometer with Cu Kα radiation at 40 kV and 40 mA. Approximately 100 mg sample was gently flattened at the center of a 50 mm diameter VeroWhitePlus sample holder for powder diffraction analysis. The sample was run as a continuous scan from 2.9° to 35° 2θ using 2θ/θ locked coupled angles with step size of 0.025° 2θ and data collection time of 0.4 seconds per step. The sample run was carried out under ambient conditions, and all data analysis was performed using EVA version 9.0 software.

Example 11. Dissolution of Compound 1 Crystalline Form I and Compound 1 Crystalline Form A in Water/DMSO at 60° C.

A solution of DMSO/water with known water content was added to a glass vial and heated to 60° C. Crystals of Compound 1 Crystalline Form I or Compound 1 Crystalline Form A were added to the vial until a suspension was obtained. The suspension was stirred via magnetic stirring and incubated for 24 hrs at 60° C. After incubation, the suspension was filtered at 60° C. 10 µL of the filtrate was sampled and diluted with 990 µL of acetonitrile/water (1/1, v/v). Sample concentration of Compound 1 was determined by HPLC. At 60° C., the solubility of Compound 1 Crystalline Form I in water/DMSO was lower than the solubility of Compound 1 Crystalline Form A in water/DMSO (FIG. 7). The experimental solubility results are summarized below in Tables 5 and 6.

TABLE 5

Solubility of Compound 1 Crystalline Form I in Water/DMSO at 60° C.

| % Water by volume | Solubility (mg/mL) |
|---|---|
| 0 | 134.0 |
| 3 | 108.0 |
| 4 | 92.15 |
| 4.5 | 74.80 |
| 6 | 65.82 |
| 8 | 34.82 |

TABLE 6

Solubility of Compound 1 Crystalline Form A in Water/DMSO at 60° C.

| % Water by volume | Solubility (mg/mL) |
|---|---|
| 0 | 153.8 |
| 6 | 73.4 |
| 8.5 | 51.0 |
| 8.7 | 44.0 |
| 9.8 | 38.5 |
| 10.7 | 32.1 |
| 11.3 | 28.6 |
| 11.8 | 25.7 |

Example 12. Screening for Fillers for Pharmaceutical Compositions Comprising Compound 1 Crystalline Form I The following fillers were evaluated for compatibility with Compound 1 Crystalline Form I:
Lactose (FlowLac 100® [Mutchler, Inc; Harrington Park, N.J., USA])
Mannitol (Pearlitol 100SD® [Roquette America, Inc; Geneva, Ill., USA])
Starch 1500 (StarCap 1500® [Colorcon, Inc; Harleysville, Pa., USA])
Dicalcium phosphate anhydrous (A-Tab® [Innophus, Inc; Cranbury, N.J., USA])

Because Compound 1 epimerization is catalyzed in the presence of an acid, 10% L-glutamic acid was included in the evaluated blends to facilitate the development of a stability indicating assay. The formulation compositions used for the study are described in Table 7. To evaluate stability, the blends were stored at the accelerated conditions of 60° C./75% RH for two weeks. A blend containing no filler but an equivalent amount of acid was used as a control in the stability indicating assay. The results from the compatibility study are shown in Table 8.

TABLE 7

Composition of Blends for Filler Screening

| Component | Vendor | F1 | F2 | F3 | F4 | F5 | F6 |
|---|---|---|---|---|---|---|---|
| Compound 1 Crystalline Form 1 (micronized) | F.I.S. | 10.0 | 10.0 | 10.0 | 10.0 | 10.0 | 50.0 |
| Aerosil 200 | Evonik Industries | 1.0 | 1.0 | 1.0 | 1.0 | 1.0 | 1.0 |
| L-glutamic acid | Sigma Aldrich | 10.0 | 10.0 | 10.0 | 10.0 | 10.0 | 49.0 |
| Mannitol | Roquette | 79.0 | — | — | — | — | — |
| Lactose (Flowlac 100) | Mutchler, Inc | — | 79.0 | — | — | — | — |
| Starch 1500 | Colorcon, Inc | — | — | 79.0 | — | — | — |
| Dicalcium Phosphate anhydrous (A-tab) | Innophus | — | — | — | 79.0 | — | — |
| MCC PH101 | Asahi Kasei Corp | — | — | — | — | 79.0 | — |

MCC = microcrystalline cellulose.

TABLE 8

Accelerated Stability Results for Filler Study

| | | | Storage Condition 60° C./75% RH | | | | | |
|---|---|---|---|---|---|---|---|---|
| | Initial | | 1 week open | | 2 weeks closed | | 2 weeks open | |
| Component | Assay (%) | Enantiomer (%) | Assay (%) | Enantiomer (%) | Assay (%) | Enantiomer (%) | Assay (%) | Enantiomer (%) |
| MCC PH101 (F5) | 101.6 | 1.59 | 90.6 | 3.79 | NT | NT | NT | NT |
| Compound 1 Crystalline Form I/ L-glutamic acid (50/50) (F6) | 100.5 | 1.62 | 99.3 | 1.68 | NT | NT | NT | NT |
| Mannitol (F1) | 98.0 | 1.60 | 98.7 | 2.02 | 101.0 | 2.03 | NT | 2.25 |
| Lactose (F2) | 97.1 | 1.61 | 95.8 | 1.95 | 99.5 | 2.02 | NT | 2.08 |
| Starch (F3) | 95.2 | 1.60 | 93.2 | 2.19 | 95.8 | 1.82 | NT | 2.52 |
| Dicalcium phosphate (F4) | 97.1 | 1.60 | 99.6 | 3.81 | NT | NT | NT | NT |

MCC = microcrystalline cellulose; NT = not tested.

MCC PH101 and dicalcium phosphate showed a higher increase in the chiral impurity at 1 week and were not tested at 2 weeks. Mannitol, lactose and starch demonstrated an acceptable increase in chiral impurity at 2 weeks.

Example 13. Preparation of Capsule Formulation of Compound 1 Crystalline Form I

To prepare a capsule formulation of Compound 1 Crystalline Form I, mannitol, colloidal silicon dioxide, and Compound 1 Crystalline Form I were weighed and added to a V-blender. The powders were then mixed in the V-blender for 5 minutes at 25 rpm. The resultant blend was passed through a comil fitted with a 032R screen (810 microns) to delump Compound 1 Crystalline Form I and the excipients mannitol and colloidal silicon dioxide. The comilled blend was mixed in a V-blender for 5 minutes at 25 rpm. Blend uniformity was evaluated as part of in-process testing. The final blend was collected and encapsulated into capsules using a manual encapsulation process. Capsules were polished using manual and instrumented equipment. Polished capsules were inspected for metal contamination, weight checked, and sorted as part of in-process testing. Weight sorted capsules were bulk packaged in a high density polyethylene (HDPE) drum lined with double polyethylene bags.

Representative manufacturing batch formula to produce approximately 45,455 capsules comprising about 10 mg dose strength Compound 1 Crystalline Form I, approximately 45,000 capsules comprising about 25 mg dose strength Compound 1 Crystalline Form I, and approximately 28,125 capsules comprising about 80 mg dose strength Compound 1 Crystalline Form I are provided in Table 9. As used herein, the dosage strength or dose strength for the capsule is represented by the approximate weight of the active drug substance (Compound 1 Crystalline Form I).

TABLE 9

Manufacturing Batch Formula for Capsules Comprising Compound 1 Crystalline Form I

| Ingredient | Amount for 45,455 units of 10 mg dose strength | Amount for 45,000 units of 25 mg dose strength | Amount for 28,125 units of 80 mg dose strength |
|---|---|---|---|
| Compound 1 Crystalline Form I[a] | 454.55 g | 1125.00 g | 2250.00 g |
| Mannitol[b] | 4495.45 g | 3330.00 g | 2205.00 g |
| Colloidal silicon dioxide | 50.00 g | 45.00 g | 45.00 g |
| Capsule shells | 1727.27 g | 1710.00 g | 1350.00 g |

[a]Actual weight adjusted based on a drug substance assay and moisture content to give the desired potency per capsule.
[b]Actual amount adjusted based on the amount of Compound 1 Crystalline Form I used to give the desired potency per capsule.

Example 14. Single Crystal X-Ray Diffraction

Crystallographic parameters of Compound 1 crystalline forms are summarized in Table 10. In the X-ray crystal structure of Compound 1 Crystalline Form, a water molecule is located on the 2-fold symmetry axis. Therefore, an asymmetric unit cell contains a molecule of 2-[(2S)-1-azabicyclo[2.2.2]oct-2-yl]-6-(3-methyl-1H-pyrazol-4-yl)thieno[3,2-d]pyrimidin-4(3H)-one and half of one water molecule. On the other hand, an asymmetric unit cell in the crystal structure of Compound 1 Crystalline Form I contains two molecules of 2-[(2S)-1-azabicyclo[2.2.2]oct-2-yl]-6-(3-methyl-1H-pyrazol-4-yl)thieno[3,2-d]pyrimidin-4(3H)-one with different conformations from each other and one water molecule. The asymmetric unit cells suggest that Compound 1 Crystalline Form A and Compound 1 Crystalline Form I are hemihydrates.

Oak Ridge Thermal Ellipsoid Program (ORTEP) figures of Compound 1 Crystalline Form I and Compound 1 Crystalline Form A are shown in FIGS. 8 and 9, respectively.

TABLE 10

Crystallographic Parameters of Compound 1 Crystals

| Crystal Form | Form A | Form I |
|---|---|---|
| Temperature | 298 K | 298 K |
| Molecular formula | $C_{17}H_{19}N_5OS \cdot 0.5H_2O$ | $C_{17}H_{19}N_5OS \cdot 0.5H_2O$ |
| Molecular weight | 349.43 | 349.43 |
| Crystal color and shape | colorless, platelet | colorless, prism |
| Crystal system | Monoclinic | monoclinic |
| Lattice parameter | a = 12.031(2) Å | 6.2263(1) Å |
| | b = 6.2460(8) Å | 43.5007(8) Å |
| | c = 21.947(4) Å | 6.7944(2) Å |
| | β = 95.26(1)° | 117.207(2)° |
| | V = 1642.3(4) | 1636.65(6) Å$^3$ |
| Space group | C2 (#5) | P2$_1$ (#4) |
| Z | | 4 |
| R (I > 2.00σ(I)) | 0.1253 | 0.0594 |
| R$_w$ | 0.3662 | 0.1502 |
| Flack χ | 0.04(7) | 0.004(18) |

Furthermore, X-ray structure analysis was also conducted using another crystal with higher quality and refinement calculations was performed using SHELXL-2014. Hydrogen atom of water was successfully identified in the new difference Fourier maps while its location could not be determined in previous maps due to low data quality. The hydrogen atoms of a methyl group and water were located in a difference Fourier synthesis and the others were placed geometrically. All hydrogen atoms were refined using a riding model. Final optimized parameter is shown in Table 11.

TABLE 11

Optimized Crystallographic Parameters of Compound 1 Crystals

| | Form A | Form I |
|---|---|---|
| Temperature | 298 K | 298 K |
| Molecular formula | $C_{17}H_{19}N_5OS \cdot 0.5H_2O$ | $C_{17}H_{19}N_5OS \cdot 0.5H_2O$ |
| Molecular weight | 350.44 | 350.44 |
| Crystal system | monoclinic | monoclinic |
| a (Å) | 12.0363(4) | 6.23273(11) |
| b (Å) | 6.2487(2) | 43.4973(8) |
| c (Å) | 21.9410(7) | 6.79041(13) |
| β (°) | 95.381(7) | 117.212(8) |
| V (Å$^3$) | 1642.95(10) | 1637.18(13) |
| Space group | C2 | P2$_1$ |
| Z | 4 | 4 |
| R (I > 2σ(I)) | 0.0692 | 0.0372 |
| Rw | 0.2193 | 0.0927 |
| Flack | 0.136(11) | 0.030(8) |

Example 15. Preparation of Compound I Crystalline Form I from Crude Compound I Crude compound 1 (16.0 kg) was dissolved in DMSO (144 L, 9.0 mL DMSO/g Compound 1). The solution was heated to 60° C. The reaction mixture was polish filtered while maintaining a mixture temperature of approximately 60° C. The transfer lines were rinsed with DMSO (11.2 L, 0.7 mL DMSO/g Compound 1). The Compound 1 solution and the rinse solution were combined. The Compound 1 solution was then heated to 60° C. Preheated 60° C. water (6.9 L, 0.43 mL water/g Compound 1) was added to the Compound 1 solution over 1 hr while maintaining an internal temperature of 60° C. Compound 1 Crystalline Form I (190.0 g, 1.2 weight %) seed crystals were charged to the reaction mixture. The reaction mixture was stirred at 60° C. for 1 hr. Preheated 60° C. water (6.5 L, 0.41 mL water/g Compound 1) was added to the Compound 1 suspension over 3 hrs while maintaining a batch temperature of 60° C. Upon completion of water addition, the slurry was stirred at 60° C. for a minimum of 4.5 hrs. A sample was taken from the slurry and filtered to obtain crystals. The crystals were analyzed by XRPD. If the sample crystals were not all Compound 1 Crystalline Form I, the stirring was continued. Samples were taken then analyzed every 6 hrs until Compound 1 Crystalline Form A was not detected by XRPD in the sample crystals. The reaction was cooled to 25° C. in 5 hrs. The solids were filtered and washed with 3 vol of 2:1/acetone:water (48 L) twice. The solids were dried under vacuum at 60° C. for 18 hrs to afford 9.5 kg (59.0% yield) of the desired product. The desired product was obtained as a white solid. HPLC showed the obtained product was >99% purity and chiral HPLC showed 97.1% ee. Analysis by XRPD confirmed the obtained product was Compound 1 Crystalline Form I.

While the foregoing disclosure has been described in some detail for purposes of clarity and understanding, these particular examples are to be considered as illustrative and not restrictive. It will be appreciated by one skilled in the art from a reading of this disclosure that various changes in form and detail can be made without departing from the true scope of the disclosure, which is to be defined by the appended claims rather than by the specific examples.

Unless otherwise defined, all technical and scientific terms used herein have the same meaning as commonly understood by one of ordinary skill in the art to which this disclosure belongs. In the case of inconsistencies, the present disclosure, including definitions, will control.

What is claimed is:

1. A crystalline form of 2-[(2S)-1-azabicyclo[2.2.2]oct-2-yl]-6-(3-methyl-1H-pyrazol-4-yl)thieno[3,2-d]pyrimidin-4(3H)-one hemihydrate (Compound 1), or a tautomer or a combination thereof, wherein Compound 1 is represented by the structure

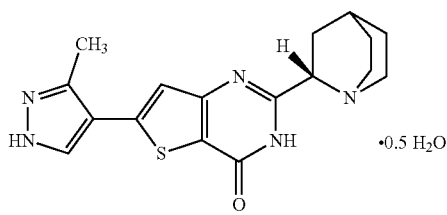

(Compound 1)

wherein the crystalline form of Compound 1 is characterized by an X-ray powder diffraction pattern having characteristic peaks expressed in degrees 2θ at 15.2±0.2, 17.8±0.2, and 27.6±0.2.

2. The crystalline form of claim 1, wherein the crystalline form characterized by an X-ray powder diffraction pattern having characteristic peaks expressed in degrees 2θ at 4.1±0.2, 8.1±0.2, 12.2±0.2, 15.2±0.2, 16.3±0.2, 17.8±0.2, and 27.6±0.2.

3. The crystalline form of claim 1, wherein the crystalline form is characterized by an X-ray powder diffraction pattern having characteristic peaks expressed in degrees 2θ at 4.1±0.2, 8.1±0.2, 12.2±0.2, 15.2±0.2, 16.3±0.2, 17.8±0.2, 19.0±0.2, and 27.6±0.2.

4. The crystalline form of claim 1, wherein the crystalline form is characterized by an X-ray powder diffraction pattern having characteristic peaks expressed in Angstroms at interplanar spacings (d) 21.6±0.2, 10.9±0.2, 7.3±0.2, 5.8±0.2, 5.4±0.2, 5.0 ±0.2, and 3.2±0.2.

5. The crystalline form of claim 1, wherein the crystalline form is characterized by an X-ray power diffraction pattern having characteristic peaks expressed in Angstroms at interplanar spacings (d) of 21.6±0.2, 10.9±0.2, 7.3±0.2, 5.8±0.2, 5.4±0.2, 5.0±0.2, 4.3±0.2, 3.4±0.2, 3.3±0.2, 3.2±0.2, and 2.9±0.2.

6. The crystalline form of claim 1, wherein the crystalline form is characterized by a solid-state $^{13}$C NMR pattern including characteristic peaks expressed in ppm at 32.2±0.5, 30.2±0.5, 29.3±0.5, 28.2±0.5, 25.3±0.5, and 24.8±0.5.

7. The crystalline form of claim 1, wherein the crystalline form is characterized by a solid-state $^{13}$C NMR pattern including characteristic peaks expressed in ppm at 159.7±0.5, 158.4±0.5, 145.1±0.5, 144.8±0.5, 140.6±0.5, 135.7±0.5, 135.3±0.5, 121.2±0.5, 114.7±0.5, 114.5±0.5, 60.4±0.5, 53.8±0.5, 46.5±0.5, 32.2±0.5, 30.2±0.5, 29.3±0.5, 28.2±0.5, 25.3±0.5, 24.8±0.5, and 14.5±0.5.

8. A pharmaceutical composition comprising the crystalline form of claim 1.

9. The pharmaceutical composition of claim 8, further comprising at least one filler chosen from mannitol or lactose.

10. The pharmaceutical composition of claim 9, wherein the filler is present in an amount ranging from 49 to 90 wt % of the pharmaceutical composition.

11. The pharmaceutical composition of claim 8, further comprising colloidal silicon dioxide.

12. The pharmaceutical composition of claim 11, wherein the colloidal silicon dioxide is present in an amount ranging from 1 to 4 wt % of the pharmaceutical composition.

13. A method for inhibiting a cell division cycle 7 in a mammal comprising administering an effective amount of the crystalline form of claim 1 to the mammal.

14. A method for treating cancer in a mammal comprising administering an effective amount of the crystalline form of claim 1 to the mammal, wherein said cancer is mediated by cell division cycle 7.

15. A process for preparing of the crystalline form of claim 1, wherein the process comprises:
   i. (A1-1a) mixing Compound 1 in DMSO to form a solution and heating the solution to a temperature ranging from 50° C. to 60° C.;
   ii. (A1-1b) optionally filtering the solution;
   iii. (A1-2) adding water preheated to a temperature ranging from 50° C. to 60° C. to the solution to form a mixture while maintaining an internal temperature of the mixture ranging from 50° C. to 60° C.;

iv. (A1-3) seeding the mixture from Step (A1-2) with a seed of Compound 1 in the crystalline form to form a first seeded mixture;

v. (A1-4) adding water preheated to a temperature ranging from 50° C. to 60° C. to the first seeded mixture to form a second seeded mixture, while maintaining an internal temperature of the second seeded mixture ranging from 50° C. to 60° C. and stirring the second seeded mixture at a temperature ranging from 50° C. to 60° C.;

vi. (A1-5) ageing the second seeded mixture resulting from Step (A1-4) to provide Compound 1 in the crystalline form.

16. The process of claim 15, wherein the total amount of DMSO present in any one of steps (A1-1a) to (A1-5) is from 9.6 to 10.6 mL DMSO per gram of Compound 1.

17. The process of claim 15, wherein the amount of the water present in any one of steps (A1-1a) to (A1-5) is from 0 to 8 wt % relative to the total amount of water and DMSO.

18. The process of claim 15, wherein the amount of the water in step (A1-3) is from 3.5 to 4.3 wt % relative to the total amount of water and DMSO.

19. The process of claim 15, wherein the particle size distribution for the seed of step (A1-3) is characterized by a D10 from 2 to 6 μm, D50 from 9 to 32 μm, or D90 from 32 to 62 μm.

20. The process of claim 15, wherein the amount of the seed added in step (A1-3) is from 0.5 to 1.0 wt % relative to the total amount of Compound 1.

* * * * *